(12) United States Patent
Ladner et al.

(10) Patent No.: US 8,124,586 B2
(45) Date of Patent: *Feb. 28, 2012

(54) PREVENTION AND REDUCTION OF BLOOD LOSS

(75) Inventors: Robert C. Ladner, Ijamsville, MD (US); Arthur C. Ley, Newton, MA (US); Shirish Hirani, Arlington, MA (US); Anthony Williams, Melrose, MA (US)

(73) Assignee: Dyax Corp., Cambridge, MA (US)

( * ) Notice: Subject to any disclaimer, the term of this patent is extended or adjusted under 35 U.S.C. 154(b) by 539 days.

This patent is subject to a terminal disclaimer.

(21) Appl. No.: 11/929,729

(22) Filed: Oct. 30, 2007

(65) Prior Publication Data

US 2008/0076712 A1    Mar. 27, 2008

Related U.S. Application Data

(63) Continuation of application No. 11/796,272, filed on Apr. 27, 2007, now abandoned, which is a continuation of application No. 11/322,960, filed on Dec. 30, 2005, now abandoned, which is a continuation of application No. 10/456,986, filed on Jun. 6, 2003, now Pat. No. 7,064,107.

(60) Provisional application No. 60/407,003, filed on Aug. 28, 2002, provisional application No. 60/387,239, filed on Jun. 7, 2002.

(51) Int. Cl.
*A61K 38/16* (2006.01)
*C07K 14/00* (2006.01)

(52) U.S. Cl. .............. 514/12; 514/2; 530/300; 530/324; 424/9.1

(58) Field of Classification Search ................ 514/2, 12; 530/324, 300; 424/9.1
See application file for complete search history.

(56) References Cited

U.S. PATENT DOCUMENTS 3,691,016 A    9/1972    Patel
(Continued)

FOREIGN PATENT DOCUMENTS

AT    E 275583 A1    4/2005
(Continued)

OTHER PUBLICATIONS

Adelman et al., "Proteolysis of Platelet Glycoprotein Ib by Plasmin Is Facilitated by Plasmin Lysine-Binding Regions," *Blood*, 68:1280-1284 (1986).
(Continued)

*Primary Examiner* — Chih-Min Kam
(74) *Attorney, Agent, or Firm* — Lando & Anastasi, LLP

(57) ABSTRACT

Methods are described for preventing or reducing ischemia and/or systemic inflammatory response in a patient such as perioperative blood loss and/or systemic inflammatory response in a patient subjected to cardiothoracic surgery, e.g. coronary artery bypass grafting and other surgical procedures, especially when such procedures involve extra-corporeal circulation, such as cardiopulmonary bypass.

17 Claims, 4 Drawing Sheets

U.S. PATENT DOCUMENTS

| | | | |
|---|---|---|---|
| 3,969,287 A | 7/1976 | Jaworek et al. | |
| 4,118,481 A | 10/1978 | Schnabel et al. | |
| 4,153,687 A | 5/1979 | Schnabel et al. | |
| 4,179,337 A | 12/1979 | Davis et al. | |
| 4,195,128 A | 3/1980 | Hildebrand et al. | |
| 4,229,537 A | 10/1980 | Hodgins et al. | |
| 4,247,642 A | 1/1981 | Hirohara et al. | |
| 4,330,440 A | 5/1982 | Ayers et al. | |
| 4,609,725 A | 9/1986 | Brady et al. | |
| 5,223,409 A | 6/1993 | Ladner et al. | |
| 5,372,933 A | 12/1994 | Zamarron | |
| 5,441,931 A | 8/1995 | Sprecher et al. | |
| 5,444,156 A | 8/1995 | Veloso et al. | |
| 5,576,294 A | 11/1996 | Norris et al. | |
| 5,635,187 A | 6/1997 | Bathurst et al. | |
| 5,677,146 A | 10/1997 | Sprecher et al. | |
| 5,719,041 A | 2/1998 | Lazarus et al. | |
| 5,747,449 A | 5/1998 | Lasters et al. | |
| 5,770,568 A | 6/1998 | Auerswald et al. | |
| 5,780,265 A | 7/1998 | Dennis et al. | |
| 5,786,328 A | 7/1998 | Dennis et al. | |
| 5,795,865 A | 8/1998 | Markland et al. | |
| 5,795,954 A | 8/1998 | Lazarus et al. | |
| 5,800,385 A | 9/1998 | Demopulos et al. | |
| 5,834,244 A | 11/1998 | Dennis et al. | |
| 5,843,895 A | 12/1998 | Lazarus et al. | |
| 5,863,893 A | 1/1999 | Dennis et al. | |
| 5,874,407 A | 2/1999 | Kelley et al. | |
| 5,880,256 A | 3/1999 | Dennis et al. | |
| 5,962,266 A | 10/1999 | White et al. | |
| 5,994,125 A | 11/1999 | Markland et al. | |
| 6,004,579 A | 12/1999 | Bathurst et al. | |
| 6,010,880 A | 1/2000 | Markland et al. | |
| 6,013,763 A | 1/2000 | Braisted et al. | |
| 6,057,287 A | 5/2000 | Markland et al. | |
| 6,071,723 A | 6/2000 | Markland et al. | |
| 6,087,473 A | 7/2000 | Conklin et al. | |
| 6,090,916 A | 7/2000 | Vlasuk et al. | |
| 6,103,499 A | 8/2000 | Markland et al. | |
| 6,113,896 A | 9/2000 | Lazarus et al. | |
| 6,159,938 A | 12/2000 | Gyorkos et al. | |
| 6,180,607 B1 | 1/2001 | Davies et al. | |
| 6,261,279 B1 | 7/2001 | Demopulos et al. | |
| 6,306,884 B1 | 10/2001 | Buckman et al. | |
| 6,333,402 B1 | 12/2001 | Markland et al. | |
| 6,423,498 B1 | 7/2002 | Markland et al. | |
| 7,064,107 B2 | 6/2006 | Ladner et al. | |
| 7,153,829 B2 | 12/2006 | Ladner et al. | |
| 7,166,576 B2 | 1/2007 | Cicardi et al. | |
| 7,235,530 B2 | 6/2007 | Blair et al. | |
| 7,276,480 B1 | 10/2007 | Ladner et al. | |
| 7,718,617 B2 | 5/2010 | Cicardi et al. | |
| 2001/0027180 A1 | 10/2001 | Isaacs | |
| 2004/0038893 A1 | 2/2004 | Ladner et al. | |
| 2004/0053206 A1 | 3/2004 | Cicardi et al. | |
| 2004/0171794 A1 | 9/2004 | Ladner et al. | |
| 2005/0164928 A1 | 7/2005 | Ladner et al. | |
| 2006/0069020 A1 | 3/2006 | Blair et al. | |
| 2007/0049522 A1 | 3/2007 | Ladner et al. | |
| 2007/0213275 A1 | 9/2007 | Clark et al. | |
| 2007/0249807 A1 | 10/2007 | Ladner et al. | |
| 2008/0064637 A1 | 3/2008 | Ladner et al. | |
| 2008/0131426 A1 | 6/2008 | Ladner et al. | |
| 2008/0139473 A1 | 6/2008 | Ladner et al. | |
| 2008/0152656 A1 | 6/2008 | Ladner et al. | |
| 2008/0188409 A1 | 8/2008 | Blair et al. | |
| 2008/0200646 A1 | 8/2008 | Ladner et al. | |
| 2008/0221031 A1 | 9/2008 | Blair et al. | |
| 2008/0226655 A1 | 9/2008 | Ladner et al. | |
| 2008/0260752 A1 | 10/2008 | Ladner et al. | |
| 2009/0082267 A1 | 3/2009 | Ladner et al. | |

FOREIGN PATENT DOCUMENTS

| | | |
|---|---|---|
| CA | 2 180 950 A1 | 3/2005 |
| DE | 695 33 472 A2 | 1/2006 |
| EP | 0 285 123 A2 | 10/1988 |
| EP | 0 621 870 B1 | 5/1997 |
| EP | 0 621 871 B1 | 7/1997 |
| EP | 739 355 B1 | 9/2004 |
| EP | 1 484 339 A2 | 12/2004 |
| WO | WO8910374 A1 | 11/1989 |
| WO | WO9206111 A1 | 4/1992 |
| WO | WO9309233 A2 | 5/1993 |
| WO | WO 93/14120 | 7/1993 |
| WO | WO 93/14121 | 7/1993 |
| WO | WO 93/14122 | 7/1993 |
| WO | WO9518830 A2 | 7/1995 |
| WO | WO 95/21601 | 8/1995 |
| WO | WO99/63090 A1 | 12/1999 |
| WO | WO0179480 A1 | 10/2001 |
| WO | WO03066824 A1 | 8/2003 |
| WO | WO 03/103475 A2 | 12/2003 |
| WO | WO 2004/019968 A1 | 3/2004 |
| WO | 2006066878 A1 | 6/2006 |
| WO | 2006089005 A2 | 8/2006 |
| WO | 2009026334 A2 | 2/2009 |

OTHER PUBLICATIONS

Albrecht et al., "Elastase Inhibition by the Inter-α-Trypsin Inhibitor and Derived Inhibitors of Man and Cattle," *Hoppe-Seyler's Z Physiol. Chem.*, 364:1697-1702 (1983).

Albrecht el al., "Kunitz-Type Proteinase Inhibitors Derived by Limited Proteolysis of the Inter-α-Trypsin Inhibitor, IX[1-8]," *Hoppe-Seyler's Z Physiol. Chem.*, 364:1703-1708 (1983).

Anba et al., "Improving the stability of a foreign protein in the periplasmic space of *Escherichia coli*," *Biochimie*, 70:727-733 (1988).

Angliker et al., "The synthesis of lysylfluoromethanes and their properties as inhibitors of trypsin, plasmin and cathepsin B," *Biochem. J.*, 241:871-875 (1987).

Atherton et al., "Peptide synthesis. Part 2. Procedures for Solid-phase Synthesis using Nα-Fluorenylmethoxycarbonylamino-acids on Polyamide Supports. Synthesis of Substance P and of Acyl Carrier Protein 65-74 Decapeptide," *J. Chem. Soc. Perkin Trans.*, 1:538-546 (1981).

Auerswald et al., "Expression, Isolation and Characterization of Recombinant [Arg$^{15}$,Glu$^{52}$] Aprotinin," *Bio. Chem. Hoppe-Seyler*, 369:(Suppl)27-35 (1988).

Balduyck et al., "Human Urinary Proteinase Inhibitor: Inhibitory Properties and Interaction with Bovine Trypsin," *Bio. Chem. Hoppe-Seyler*, 366:9-14 (1985).

Baneyx and Georgiou, "In Vivo Degradation of Secreted Fusion Proteins by the *Escherichia coli* Outer Membrane Protease OmpT" *J. Bacterial.*, 172:491-494 (1990).

Baneyx and Georgiou, "Construction and Characterization of *Escherichia coli* Strains Deficient in Multiple Secreted Proteases: Protease III Degrades High-Molecular-Weight Substrates In Vivo," *J. Bacterial.*, 173:2696-2703 (1991).

Berndt et al., "Designed Replacement of an Internal Hydration Water Molecule in BPTI: Structural and Functional Implications of a Glycine-to-Serine Mutation," *Biochem.*, 32:4564-4570 (1993).

Bhoola et al., "Bioregulation of Kinins: Kallikreins, Kininogens, and Kininases," *Pharmacological Reviews*, 44:1-80 (1992).

Browne et al., "Expression of Recombinant Human Plasminogen and Aglycoplasminogen in HeLa Cells," *GeneBank*, Accession No. M74220 (1991).

Broze et al., "Regulation of Coagulation by a Multivalent Kunitz-Type Inhibitor," *Biochem.*, 29:7539-7546 (1990).

Brus et al., "Disease Severity is Correlated With Plasma Clotting and Fibrinolytic and Kinin-Kallikrein Activity in Neonatal Respiratory Distress Syndrome," *Pediatr. Res.*, 41:120-127 (1997).

Budavari, ed., Merck Index, 11$^{th}$ Edition, ISBN 911910-28-X, entries 923, 1745, 2740, 7425 (1989).

Chung et al., "Human Plasma Prekallikrein, a Zymogen to a Serine Protease That Contains Four Tandem Repeats," *GenBank*, Accession No. P03952 (1995).

Colman et al., "Activation of the Kallikrein-Kinin System in Arthritis and Enterocolitis in Genetically Susceptible Rats: Modulation by a Selective Plasma Kallikrein Inhibitor," *Proc. Assoc. Am. Physicians*, 109:10-22 (1997).

Cumming and Nimmo, "Hemodynamic, Renal, and Hormonal Actions of Aprotinin in an Ovine Model of Septic Shock," *Crit. Care Med.*, 20:1134-1139 (1992).

Currie, B. "Design and Synthesis of a Bicyclic Non-Peptide β-Bend Mimetic of Enkephalin," *Tetrahedron*, 49:3489-3500 (1993).

DeLa Cadena et al., "Role of Kallikrein-Kinin System in the Pathogenesis of Bacterial Cell Wall-Induced Inflammation and Enterocolitis," *Transact. Assoc. Am. Physicians*, 105:229-237 (1992).

DeLa Cadena et al., "Inhibition of Plasma Kallikrein Prevents Peptidoglycan-induced Arthritis in the Lewis Rat," *FASEB J.*, 9:446-452 (1995).

Dennis and Lazarus, "Kunitz Domain Inhibitors of Tissue Factor-Factor VIIa, (I. Potent Inhibitors Selected from Libraries by Phage Display)," *J. Biol. Chem.*, 269:22129-22136 (1994).

Dennis and Lazarus, "Kunitz Domain Inhibitors of Tissue Factor-Factor VIIa, (II. Potent and Specific Inhibitors by Competitive Phage Selection)," *J. Biol. Chem.*, 269:22137-22144 (1994).

Dennis el al., "Potent and Selective Kunitz Domain Inhibitors of Plasma Kallikrein Designed by Phage Display," *J. Biol. Chem.*, 270:25411-25417 (1995).

Diaz et al., "The Design of Water Soluble β-Sheet Structure Based on a Nucleation Strategy," *Tetrahedron*, 49:3533-3534 (1993).

DiMaio et al., "A new class of potent thrombin inhibitors that incorporates a scissile pseudopeptide bond," *FEBS Lett.*, 282(1):47-52 (1991).

Eigenbrot et al., "Structural Effects Induced by Removal of a Disulfide-Bridge: The X-ray Structure of the C30A/C51A Mutant of Basic Pancreatic Trypsin Inhibitor at 1.6 Å,"*Protein Engineering*, 3:591-598 (1990).

Ellis et al., "The Urokinase Receptor: Involvement in Cell Surface Proteolysis and Cancer Invasion," *Ann. NY Acad. Sci.*, 667:13-31 (1992).

Fidler and Ellis, "The Implications of Angiogensis for the Biology and Therapy of Cancer Metastasis," *Cell*, 79:185-188 (1994).

Fields and Noble, "Solid Phase Peptide Synthesis Utilizing 9-fluorenylmethoxycarbonyl Amino Acids," *Int. J. Pep. Pro. Res.*, 35:161-214 (1990).

Fraedrich et al., "Reduction of Blood Transfusion Requirement in Open Heart Surgery by Administration of High Doses of Aprotinin-Preliminary Results," *Thorac. Cardiovasc. Surg.*, 37:89-91 (1989).

Freidinger et al., "Protected Lactam-Bridged Dipeptides for Use as Conformational Constraints in Peptides," *J. Org. Chem.*, 47:104-109 (1982).

Gardell, "The Search for the Ideal Thrombolytic Agent: Maximize the Benefit and Minimize the Risk," *Toxicol. Pathol.*, 21(2):190-198 (1993).

Girard et al., "Functional Significance of the Kunitz-type Inhibitory Domains of Lipoprotein-Associated Coagulation Inhibitor," *Nature*, 338:518-520 (1989).

Girard et al., "Structure of the Human Lipoprotein-associated Coagulation Inhibitor Gene," *J. Biol. Chem.*, 266:5036-5041 (1991).

Hoover et al., "Amino Acids of the Recombinant Kringle 1 Domain of Human Plasminogen That Stabilize Its Interaction with ω-Amino Acids," *Biochemistry*, 32:10936-10943 (1993).

Hortin and Trimpe, "Allosteric Changes in Thrombin's Activity Produced by Peptides Corresponding to Segments of Natural Inhibitors and Substrates," *J. Biol. Chem.*, 266:6866-6871 (1991).

Hostomsky et al., "Solid-Phase Assembly of Cow Colostrum Trypsin Inhibitor Gene," *Nucleic Acids Res.*, 15:4849-4856 (1987).

Hynes et al., "X-ray Crystal Structure of the Protease Inhibitor Domain of Alzheimer's Amyloid β-Protein Precursor," *Biochemistry*, 32:10936-10943 (1993).

Kemp and Bowen, "Synthesis of Peptide-Functionalized Diacylaminoepindolidiones," *Tetrahedron Letts.*, 29:5077-5080 (1988).

Kido et al., "Protease-Specificity of Kunitz Inhibitor Domain of Alzheimer's Disease Amyloid Protein Precursor," *Biochem. & Biophys. Res. Comm.*, 167:716-721 (1990).

Kido et al., "Kunitz-type Protease Inhibitor Found in Rat Mast Cells," *J. Biol. Chem.*, 263:18104-18107 (1988).

Kirchhoff et al., "A Major Human Epididymis-Specific cDNA Encodes a Protein With Sequence Homology to Extracellular Proteinase Inhibitors," *Biol. Reprod.*, 45:350-357 (1991).

Kline et al., "Hirulog Peptides with Scissile Bond Replacements Resistant to Thrombin Cleavage," *Biochem. Biophys. Res. Commun.*, 177:1049-1055 (1991).

Kurjan and Herskowitz, "Structure of a Yeast Pheromone Gene (MFα): A Putative α-Factor Precursor Contains Four Tandem Copies of Mature α-Factor," *Cell*, 30:933-943 (1982).

Laskowski and Kato, "Inhibitors with Class-Specific Reactive Sites," *Ann. Rev. Biochem.*, 49:593-626 (1980).

Leatherbarrow and Salacinski, "Design of a Small Peptide-Based Proteinase Inhibitor by Modeling the Active-Site Region of Barley Chymotrypsin Inhibitor 2," *Biochemistry*, 30:10717-10721 (1991).

Ley et al., "Obtaining a Family of High-Affinity, High-Specificity Protein Inhibitors of Plasmin and Plasma Kallikrein," *Molecular Diversity*, 2:119-124 (1996).

Lohmann and Marshall, "Plasmin-and Plasminogen-Activator Inhibitors After Excimer Laser Photorefractive Keratectomy: New Concept in Prevention of Postoperative Myopic Regression and Haze," *Refract. Corneal. Surg.*, 9:300-302 (1993).

Lucas et al., "The Binding of Human Plasminogen to Fibrin and Fibrinogen," *J. Biol. Chem.*, 258:4249-4256 (1983).

MacGilchrist et al., "Effect of the Serine Protease Inhibitor, Aprotinin, on Systemic Haemodynamics and Renal Function in Patients with Hepatic Cirrhosis and Ascites," *Clin. Sci.*, 87:329-335 (1994).

Markland et al., "Selection for Protease Inhibitors Using Bacteriophage Display," *Methods Enzymol.*, 267:28-51 (1996).

Markland et al., "Iterative Optimization of High-Affinity Protease Inhibitors Using Phage Display. 1. Plasmin," *Biochemistry*, 35:8045-8057 (1996).

Markland et al., "Iterative Optimization of High-Affinity Protease Inhibitors Using Phage Display. 2. Plasma Kallikrein and Thrombin," *Biochemistry* 35:8058-8067 (1996).

McConnell et al., "New Leupeptin Analogues: Synthesis and Inhibition Data," *J. Med. Chem.*, 33:86-93 (1990).

Merrifield, R., "Solid Phase Peptide Synthesis. 1. The Synthesis of a Tetrapeptide," *J. Amer. Chem. Soc.*, 85:2149-2154 (1963).

Merrifield, B., "Solid Phase Synthesis," *Science*, 232:341-347 (1986).

Miyajima et al., "Secretion of Mature Mouse Interleukin-2 by *Saccharomyces cerevisiae*: Use of a General Secretion Vector Containing Promoter and Leader Sequences of the Mating Pheromone α-Factor," *Gene*, 37:155-161 (1985).

Monteseirín et al., "Plasma Kallikrein Amidolytic Activity in Bronchial Asthma," *Allergol. Immunopathol. (Madr)*, 20:211-214 (1992).

Naess et al, "Effects of a Combined Drug Regimen on Tumour Necrosis Factor and Plasma Kallikrein Activity in Experimental Endotoxaemia," *Eur. J. Surg.*, 160:77-86 (1994).

Nagai et al., "Bicyclic Turned Dipeptide (BTD) as a β-Turn Mimetic: its Design, Synthesis and Incorporation into Bioactive Peptides," *Tetrahedron*, 49:3577-3592 (1993).

Nagai and Sato, "Synthesis of a Bicyclic Dipeptide with the Shape of β-Turn Central Part ," *Tetrahedron Lett.*, 26(5):647-650 (1985).

Neuhaus et al., "Effect of Aprotinin on Intraoperative Bleeding and Fibrinolysis in Liver Transplantation," *Lancet*, 2:924-925 (1989).

Novotny et al., "Purification and Characterization of the Lipoprotein-Associated Coagulation Inhibitor from Human Plasma," *J. Biol. Chem.*, 264:18832-18837 (1989).

Okamoto et al., "A Finding of Highly Selective Synthetic Inhibitor of Plasma Kallikrein; Its Action to Bradykinin Generation, Intrinsic Coagulation and Experimental DIC," *Agents Actions Suppl.*, 38(I):198-205 (1992).

O'Reilly et al., "Angiostatin: A Novel Angiogenesis Inhibitor That Mediates the Suppression of Metastases by a Lewis Lung Carcinoma," *Cell*, 79:317-328 (1994).

Park and Tulinsky, "Three Dimensional Structure of the Kringle Sequence: Structure of Prothrombin Fragment 1," *Biochem.*, 25:3977-3982 (1986).

Putterman, C., "Aprotinin Therapy in Septic Shock," *Acta Chir. Scand.*, 155:367 (1989).

Sartor et al., "Selective Kallikrein-Kinin System Activation in Inbred Rats Differentially Susceptible to Granulomatous Enterocolitis," *Gastroenterology* 110:1467-1481 (1996).

Schmidt et al., "A male accessory gland peptide with protease inhibitory activity in *Drosophila funebris*," *Swiss-Prot.*, Accession No. P11424 (1992).

Schnabel et al., "Aprotinin: Preparation by Partial Desulphurization of Aprotinin by Means of Raney Nickel and Comparison with Other Aprotinin Derivatives," *Biol. Chem. Hoppe-Seyler*, 367:1167-1176 (1986).

Sheppard and Williams, "Acid-labile resin linkage agents for use in solid phase peptide synthesis," *Int. J. Peptide Protein Res.*, 20:451-454 (1982).

Sheridan el al., "A Multicenter Trial of the Use of the Proteolytic Enzyme Inhibitor Aprotinin in Colorectal Surgery," *Dis. Colon Rectum*, 32:505-508 (1989).

Sprecher et al., "Molecular Cloning, Expression, and Partial Characterization of a Second Human Tissue-Factor-Pathway Inhibitor," *Proc. Natl., Acad. Sci. USA*, 91:3353-3357 (1994).

Stadnicki et al., "Activation of the Kallikrein-Kinin System in Indomethacin-Induced Enterocolitis in Genetically Susceptible Rats," *J. Invest. Med*, 44:229A (1996).

Stadnicki et al., "Selective Plasma Kallikrein Inhibitor Attenuates Acute Intestinal Inflammation in Lewis Rat," *Dig. Dis. Sci.*, 41:912-920 (1996).

Tian et al., "Synthesis of optically pure C°-methyl-arginine," *Int. J. Peptide Protein Res.*, 40:119-126 (1992).

van der Logt et al., "Intron-Exon Organization of the Human Gene Coding for the Lipoprotein-Associated Coagulation Inhibitor: The Factor Xa Dependent Inhibitor of the Extrinsic Pathway of Coagulation," *Biochem.*, 30:1571-1577 (1991).

van Dijl et al., "Signal peptidate I of *Bacillus subtilis*: patterns of conserved amino acids in prokaryotic and eukaryotic type I signal peptidases," *EMBO J.*, 11:2819-2828 (1992).

Varadi and Patthy, "Location of Plasminogen-Binding Sites in Human Fibrin(ogen)," *Biochem.*, 22:2440-2446 (1983).

Varadi and Patthy, "Segment of Fibrinogen is in a Region Essential for Plasminogen Binding by Fibrin Fragment E," *Biochem.*, 23:2108-2112 (1984).

Vedvick et al., "High-Level Secretion of Biologically Active Aprotinin From the Yeast *Pichia pastoris*," *J. Ind. Microbiol.*, 7:197-201 (1991).

Wade et al., "Solid-Phase Synthesis of α-Human Atrial Natriuretic Factor: Comparison of the Boc-Polystyrene and Fmoc-Polyamide Methods," *Biopolymers*, 25:S21-37 (1986).

Wagner et al., "High Level Expression, Purification, and Characterization of the Kunitz-Type Protease Inhibitor Domain of Protease Nexin-2/Amyloid β-Protein Precursor," *Biochem. Biophys. Res. Comm.*, 186:1138-1145 (1992).

Wilson et al., "The Calculation and Synthesis of a Template Molecule," *Tetrahedron*, 49:3655-3663 (1993).

Wun et al., "Cloning and Characterization of a cDNA Coding for the Lipoprotein-associated Coagulation Inhibitor Shows that it Consists of Three Tandem Kunitz-type Inhibitory Domains," *J. Biol. Chem.*, 263:6001-6004 (1988).

PCT International Search Report dated Jul. 21, 2008 and issued in PCT/US05/34335.

PCT Written Opinion dated Jul. 21, 2008 and issued in PCT/US05/34335.

Attwood, The Babel of Bioinformatics; Science, vol. 290, pp. 471-473 (2000).

Skolnick and Fetrow, From Genes to Protein Structure and Function: Novel Applications of Computational Approaches in the Genomic Era; Trends in Biotechnology, vol. 18, pp. 34-39 (2000).

Wendel et al., Lower Cardiac Troponin T Levels in Patients Undergoing Cardiopulmonary Bypass and Receiving High-Dose Aprotinin Therapy Indicate Reduction of Perioperative Myocardial Damage; Journal of Thoracic Cardiovascular Surgery, vol. 109, No. 6, pp. 1164-1172 (1995).

Baba, M et al., States of Tyrosyl Residues and Circular Dichroism of Kunitz Trypsin Inhibitor, J. Biochem 65 (1):113-121 (1969).

Carey et al., Advanced Organic Chemistry, 3rd Edition, Part B: Reactions and Synthesis, Plenum Press, New York: 678-686 (1990).

Chen et al., Solution Structure of a Kunitz-type Chymotrypsin Inhibitor Isolated from the Elapid Snake Bungarus Fasciatus, J. Biological Chemistry 276:45079-45087 (2001).

Chung et al., GenBank, Accession #P03952 (1986).

Han, Eun D. Reversal of the Increased Vascular Permeability in C1 Inhibitor Deficient Mice: Therapeutic Approaches, International Immunopharmacology 2(9):1315 Abstract 176 (2002).

Han, Eun D. et al., Increased Vascular Permeability in C1 Inhibitor-Deficient Mice Mediated by the Bradykinin Type 2 Receptor, J. Clinical Investigation 109(8):1057-1063 (2002).

Gonzalez-Quevedo, T. et al., The Synthetic Kunitz Domain Protein DX88 to Treat Angioedema in Patients with Hereditary Angioedema, International Immunopharmacology 2(9):1318 Abstract 205 (2002).

Lumry et al, Interim Results of EDEMA2, A Multicenter, Open-Label, Repeat-Dosing Study of Intravenous and Subcutaneous Administration of Ecallantide (DX-88) in Hereditory Angioedema. J. Allergy and Clinical Immunology 117(2)(Suppl. 1):S179 Abstract 699 (2006).

Mann et al., Hemostasis and Thrombosis, Chapter 10, 2nd Edition, Basic Principles and Clinical Practice: 148-161 (1987).

March, Jerry, Advanced Organic Chemistry, 3rd Edition, Reactions, Mechanisms, and Structure, John Wiley and Sons, New York: 396-398; 1057-1060; 1099-1100 (1985).

Mathews, C.K., et al., Biochemistry, The Benjamin Cummins Publishing Co., Inc. Redwood City CA: 208-212 (1990).

McConnell et al., New Leupeptin Analogues: Synthesis and Inhibition Data, J. Med. Chem. 33:86-93 (1990).

The Merck Index: 145, 263, 427, 428, 1183, and 1184 (1989).

Robbins, K.C. et al., Hemostasis and Thrombosis, Chapter 21, 2nd Edition, Basic Principles and Clinical Practice: 340-357 (1987).

Rossi, E. et al., The Synthetic Peptide DX88 Binds to Endothelial Cells In Vitro and Retains the Inhibitory Activity on Kallikrein, International Immunopharmacology 2(9):1313, Abstract 142 (2002).

Scatchard, George, The Attractions of Proteins for Small Molecules and Ions, Ann. NY Acad. Sci, 51:660-672 (1949).

Schecther et al., On the Size of the Active Site on Proteases, I Papain, Biochemical and Biophysical Research Communications 27(2):157-162 (1967).

Schecther et al, On the Active Site of Proteases, III Mapping the Active Site of Papain; Specific Peptide Inhibitors of Papain, Biochemical and Biophysical Research Communications 32(5):898-902 (1968).

Schmaier et al., Hemostasis and Thrombosis, Chapter 2, 2nd Edition, Basic Principals and Clinical Practice: 18-38 (1987).

Communication received in EP Patent No. 1 484 339, dated Sep. 29, 2005.

International Search Report received in PCT/US07/63703, dated Dec. 21, 2007.

Communication received in EP Patent Application 03757339.1, dated Apr. 23, 2008.

Bork., "Powers and Pitfalls in Sequence Analysis: The 70% Gurdle", Genome Research, vol. 10, pp. 398-400. (2000).

Doerks, et al., "Protein annotation: detective work for function prediction", Trends in Genetics, vol. 14 (6), pp. 248-250. (1998).

Ngo, et al., "Computational Complexity, Protein Structure Prediction, and the Levinthal Paradox", The Protein Folding Problem and Tertiary Structure Prediction, Chapter 14, pp. 433-440 and 492-495 only. (1994).

Wells, "Addivity of Mutational Effects in Proteins", Biochemistry, vol. 29 (37), pp. 8509-8517. (1990).

Brenner, "Errors in genome annotation" Trends in Genetics, vol. 15 (4), pp. 132-133. (1999).

Blaber, et al., "Targeting kallikrein 6-proteolysis attenuates CNS inflammatory disease" The FASEB Journal, express article published online Mar. 19, 2004.

Colman, et al., "The Plasma Kallikrein-Kinin System in Sepsis, Inflammatory Arthritis, and Enterocolitis" Clinical Reviews in Allergy and Immunology, vol. 16, pp. 365-384 (1998).

Colman, et al., Hemostasis and Thrombosis Basic Principles and Clinical Practice, Chapter 1, 2nd Edition,: 3-17 (1987).

Chen, et al. "Refined 2-5 Å X-ray Crystal Structure of the Complex Formed by Porcine Kallikrein A and the Bovine Pancreatic Trypsin Inhibitor—Crystallization, Patterson Search, Structure Determination, Refinement, Structure and Comparison with its Components and with the Bovine Trypsin-Pancreatic Trypsin Inhibitor Complex" J. Mol. Biol. vol. 164, pp. 283-311 (1983).

Wood, Alastair, J.J, "Hemostatic Drugs" New England Journal of Medicine, Drug Therapy, vol. 339, No. 4, pp. 245-253 (1998).

Extended European Search Report dated Apr. 2, 2009, which includes the European Search Report and the European Search Opinion.

Colman., "Plasma and tissue kallikrein in arthritis and inflammatory bowel disease" Immunopharmacology, vol. 43, pp. 103-108 (1999).

Worthy et al., "Current Status Review Kallikreins and Kinins: mediators in inflammatory joint disease" Int. J. Exp. Path. 71, 587-601(1990).

Bayes et al., "Gateways to Clinical Trials" Methods Find Exp. Clin. Pharmacol., vol. 28(3): pp. 185-206 (2006).

Extended European Search Report from European Application Serial No. 08798517.2 dated Nov. 2, 2010.

Extended European Search Report from European Application Serial No. 10180486.2 dated Feb. 23, 2011.

Extended European Search Report from European Application Serial No. 10180484.7 dated Mar. 9, 2011.

Figure 2

```
5AOX1
------------------------------------+              BstB I
CG ACT TTT AAC GAC AAC TTG AGA AGA TCA AAA AAC AAC TAA TTA TTC GAA

ACG     ATG AGA TTC CCA TCT ATC TTC ACT GCT GTT TTG TTC GCT GCT
        M   R   F   P   S   I   F   T   A   V   L   F   A   A

TCC TCT GCT TTG GCT GCT CCA GTT AAC ACC ACT ACT GAA GAC GAG ACT
 S   S   A   L   A   A   P   V   N   T   T   T   E   D   E   T

GCT CAA ATT CCT GCT GAG GCT GTC ATC GGT TAC TCT GAC TTG GAA GGT
 A   Q   I   P   A   E   A   V   I   G   Y   S   D   L   E   G

GAC TTC GAC GTC GCT GTT TTG CCA TTC TCT AAC TCT ACT AAC AAC GGT
 D   F   D   V   A   V   L   P   F   S   N   S   T   N   N   G

TTG TTG TTC ATC AAC ACT ACC ATC GCT TCT ATC GCT GCT AAG GAG GAA
 L   L   F   I   N   T   T   I   A   S   I   A   A   K   E   E

GGT GTT TCC CTC GAG AAG AGA GAG GCT ATG CAC TCT TTC TGT GCT TTC
 G   V   S   L   E   K   R   E   A   M   H   S   F   C   A   F

AAG GCT GAC GAC GGT CCG TGC AGA GCT GCT CAC CCA AGA TGG TTC TTC
 K   A   D   D   G   P   C   R   A   A   H   P   R   W   F   F

AAC ATC TTC ACG CGT CAA TGC GAG GAG TTC ATC TAC GGT GGT TGT GAG
 N   I   F   T   R   Q   C   E   E   F   I   Y   G   G   C   E

GGT AAC CAA AAC AGA TTC GAG TCT CTA GAG GAG TGT AAG AAG ATG TGT
 G   N   Q   N   R   F   E   S   L   E   E   C   K   K   M   C

EcoR I
ACT AGA GAC TAG TAA GAA TTC GCC TTA GAC ATG ACT GTT CCT CAG TTC
 T   R   D   *   *                                        <------
                                                           3'AOX1

AAG TTG GGC ACT TAC GAG AAG
         3'AOX1
```

FIGURE 3A

```
SEQ ID 2:   (amino acids 3-60)    ----MHSFCAFKA-DDGPCRAAHPRWFFNIFTRQCEEFIYGG
SEQ ID 4:                         ----MHSFCAFKA-DDGPCKANHLRFFFNIFTRQCEEFSYGG
SEQ ID 5:                         ----MHSFCAFKA-DDGHCKANHQRFFFNIFTRQCEEFTYGG
SEQ ID 6:                         ----MHSFCAFKA-DDGHCKANHQRFPFNIFTRQCEQFTYGG
SEQ ID 7:                         ----MHSFCAFKA-DDGHCKASLPRFFFNIFTRQCEEFIYGG
SEQ ID 8:                         ----MHSFCAFKA-DDGHCKANHQRFPFNIFTRQCEEFSYGG
SEQ ID 9:                         ----MHSFCAKFA-DDGHCKGAHLRFFFNIFTRQCEEFIYGG
SEQ ID 10:                        ----MHSFCAFKA-DDGRCKGAHLRFFFNIFTRQCEEFIYGG
SEQ ID 11:                        ----MHSFCAFKA-DGGRCRGAHPRWFFNIFTRQCEEFSYGG
SEQ ID 12:                        ----MHSFCAFKA-DDGPCRAAHPRWFFNIFTRQCEEFSYGG
SEQ ID 13:                        ----MHSFCAFKA-DVGRCRGAHPRWFFNIPTRQCEEFSYGG
SEQ ID 14:                        ----MHSFCAFKA-DVGRCRGAQPRFFFNIFTRQCEEFSYGG
SEQ ID 15:                        ----MHSFCAFKA-DDGSCRAAHLRWFFNIFTRQCEEFSYGG
SEQ ID 16:                        ----MHSFCAFKA-EGGSCRAAHQRWFFNIFTRQCEEFSYGG
SEQ ID 17:                        ----MHSFCAFKA-DDGPCRGAHLRFFFNIFTRQCEEFSYGG
SEQ ID 18:                        ----MHSFCAFKA-DDGHCRGALPRWFFNIPTRQCEEFSYGG
SEQ ID 19:                        ----MHSFCAFKA-DSGNCRGNLPRFFFNIFTRQCEEFSYGG
SEQ ID 20:                        ----MHSFCAFKA-DSGRCRGNHQRFFFNIFTRQCEEFSYGG
SEQ ID 21:                        ----MHSFCAFKA-DGGRCRAIQPRWFFNIPTRQCEEFSYGG
SEQ ID 22:                        ----MHSFCAFKA-DDGRCRGAHPRWFFNIFTRQCEEFSYGG
BPTI (SEQ ID 29):                 ----RPDFCLEPP-YTGPCKARIIRYFYNAKAGLCQTFVYGG
ITI-D1 (SEQ ID 30):               -----KEDSCQLGY-SAGPCMGMTSRYFYNGTSMACETFQYGG
ITI-D2 (SEQ ID 31):               ----TVAACNLPI-VRGPCRAFIQLWAFDAVKGKCVLFPYGG
LACI-D1 (SEQ ID 32):              ----MHSFCAFKA-DDGPCKAIMKRFFFNIFTRQCEEFIYGG
LACI-D2 (SEQ ID 33):              ----KPDFCFLEE-DPGICRGYITRYFYNNQTKQCERFKYGG
LACI-D3 (SEQ ID 34):              ----GPSWCLTPA-DRGLCRANENRFYYNSVIGKCRPFKYSG
HKI B9 (SEQ ID 35):               ----LPNVCAFPM-EKGPCQTYMTRWFFNFETGSCELFAYGG
C-3 (SEQ ID 36):                  ----ETDICKLPK-DEGTCRDFILKWYYDPNTKSCARPWYGG
TFPI-2 D1 (SEQ ID 37):            ----NAEICLLPL-DYGPCRALLLRYYYDRYTQSCRQFLYGG
TFPI-2 D2 (SEQ ID 38):            ----VPKVCRLQVSVDDQCEGSTEKYFFNLSSMTCEKFFSGG
TFPI-2 D3 (SEQ ID 39):            ----IPSFCYSPK-DEGLCSANVTRYYFNPRYRTCDAFTYTG
APP-I (SEQ ID 40):                ---RNREVCSEQA-ETGPCRAMISRWYFDVTEGKCAPFFYGG
EpiNE7 (SEQ ID 41):               ----RPDFCLEPP-YTGPCVAMFPRYFYNAKAGLCQTFVYGG
BITI-E7-141 (SEQ ID 42):          ----RPDFCQLGY-SAGPCVAMFPRYFYNGTSMACQTFVYGG
MUTT26A (SEQ ID 43):              ----RPDFCQLGY-SAGPCVAMFPRYFYNGASMACTFVYGG
MUTQE (SEQ ID 44):                ----RPDFCQLGY-SAGPCVAMFPRYFYNGTSMACETFVYGG
MUT1619 (SEQ ID 45):              ----RPDFCQLGY-SAGPCVGMFSRYFYNGTSMACQTFVYGG
EPI-HNE-1 (SEQ ID 46):            EAEARPDFCLEPP-YTGPCIAFFPRYFYNAKAGLCQTFVYGG
EPI-HNE-2 (SEQ ID 47):            ------AACNLPI-VRGPCIAFFPRWAFDAVKGKCVLFPYGG
EPI-HNE-3 (SEQ ID 48):            ------AACNLPI-VRGPCIAFFPRWAFDAVKGKCVLFPYGG
EPI-HNE-4 (SEQ ID 49):            -------EACNLPI-VRGPCIAFFPRWAFDAVKGKCVLFPYGG
DPI14 KR (SEQ ID 50):             --EAVREVCSEQA-ETGPCIAFFPRWYFDVTEGKCAPFFYGG
DPI24 KR (SEQ ID 51):             --EANAEICLLPL-DYGPCIAFFPRYYYDRYTQSCRQFLYGG
DPI68 KR (SEQ ID 52):             --EAKPDFCFLEE-DPGICIGFFPRYFYNNQAKQCERFVYGG
DPI84 KR (SEQ ID 53):             --EAETDICKLPK-DEGTCIAFFPRWYYDPNTKSCARFVYGG
```

FIGURE 3B

| | | |
|---|---|---|
| SEQ ID 2: | (cont.) | CEGNQ--NRFESLEECKKMCTRD |
| SEQ ID 4: | (cont.) | CGGNQ--NRFESLEECKKMCTRD |
| SEQ ID 5: | (cont.) | CGGNQ--NRFESLEECKKMCTRD |
| SEQ ID 6: | (cont.) | CAGNQ--NRFESLEECKKMCTRD |
| SEQ ID 7: | (cont.) | CGGNQ--NRFESLEECKKMCTRD |
| SEQ ID 8: | (cont.) | CGGNQ--NRFESLEECKKMCTRD |
| SEQ ID 9: | (cont.) | CEGNQ--NRFESLEECKKMCTRD |
| SEQ ID 10: | (cont.) | CEGNQ--NRFESLEECKKMCTRD |
| SEQ ID 11: | (cont.) | CGGNQ--NRFESLEECKKMCTRD |
| SEQ ID 12: | (cont.) | CGGNQ--NRFESLEECKKMCTRD |
| SEQ ID 13: | (cont.) | CGGNQ--NRFESLEECKKMCTRD |
| SEQ ID 14: | (cont.) | CGGNQ--NRFESLEECKKMCTRD |
| SEQ ID 15: | (cont.) | CGGNQ--NRFESLEECKKMCTRD |
| SEQ ID 16: | (cont.) | CGGNQ--NRFESLEECKKMCTRD |
| SEQ ID 17: | (cont.) | CGGNQ--NRFESLEECKKMCTRD |
| SEQ ID 18: | (cont.) | CGGNQ--NRFESLEECKKMCTRD |
| SEQ ID 19: | (cont.) | CGGNQ--NRFESLEECKKMCTRD |
| SEQ ID 20: | (cont.) | CGGNQ--NRFESLEECKKMCTRD |
| SEQ ID 21: | (cont.) | CGGNQ--NRFESLEECKKMCTRD |
| SEQ ID 22: | (cont.) | CGGNQ--NRFESLEECKKMCTRD |
| BPTI (SEQ ID 29): | (cont.) | CRAKR--NNFKSAEDCMRTCGGA |
| ITI-D1 (SEQ ID 30): | (cont.) | CMGNG--NNFVTEKECLQTCRTV |
| ITI-D2 (SEQ ID 31): | (cont.) | CQGNG--NKFYSEKECREYCGVP |
| LACI-D1 (SEQ ID 32): | (cont.) | CEGNQ--NRFESLEECKKMCTRD |
| LACI-D2 (SEQ ID 33): | (cont.) | CLGNM--NNFETLEECKNICEDG |
| LACI-D3 (SEQ ID 34): | (cont.) | CGGNE--NNFTSKQECLRACKKG |
| HKI B9 (SEQ ID 35): | (cont.) | CGGNS--NNFLRKEKCEKFCKPT |
| C-3 (SEQ ID 36): | (cont.) | CGGNE--NKFGSQKECEKVCAPV |
| TFPI-2 D1 (SEQ ID 37): | (cont.) | CEGNA--NNFYTWEACDDACWRI |
| TFPI-2 D2 (SEQ ID 38): | (cont.) | CHRNRIENRFPDEATCMGFCAPK |
| TFPI-2 D3 (SEQ ID 39): | (cont.) | CGGND--NNFVSREDCKRACAKA |
| APP-I (SEQ ID 40): | (cont.) | CGGNR--NNFDTEEYCMAVCGSA |
| EpiNE7 (SEQ ID 41): | (cont.) | CMGNG--NNFKSAEDCMRTCGGA |
| BITI-E7-141 (SEQ ID 42): | (cont.) | CMGNG--NNFVTEKDCLQTCRGA |
| MUTT26A (SEQ ID 43): | (cont.) | CMGNG--NNFVTEKDCLQTCRGA |
| MUTQE (SEQ ID 44): | (cont.) | CMGNG--NNFVTEKDCLQTCRGA |
| MUT1619 (SEQ ID 45): | (cont.) | CMGNG--NNFVTEKDCLQTCRGA |
| EPI-HNE-1 (SEQ ID 46): | (cont.) | CMGNG--NNFKSAEDCMRTCGGA |
| EPI-HNE-2 (SEQ ID 47): | (cont.) | CQGNG--NKFYSEKECREYCGVP |
| EPI-HNE-3 (SEQ ID 48): | (cont.) | CQGNG--NKFYSEKECREYCGVP |
| EPI-HNE-4 (SEQ ID 49): | (cont.) | CQGNG--NKFYSEKECREYCGVP |
| DPI14 KR (SEQ ID 50): | (cont.) | CGGNR--NNFDTEEYCMAVCGSA |
| DPI24 KR (SEQ ID 51): | (cont.) | CEGNA--NNFYTWEACDDACWRI |
| DPI68 KR (SEQ ID 52): | (cont.) | CLGNM--NNFETLEECKNICEDG |
| DPI84 KR (SEQ ID 53): | (cont.) | CGGNE--NKFGSQKECEKVCAPV |

PREVENTION AND REDUCTION OF BLOOD LOSS

RELATED APPLICATION

This application is a continuation of U.S. application Ser. No. 11/796,272, filed Apr. 27, 2007, now abandoned, which is a continuation of U.S. application Ser. No. 11/322,960, filed Dec. 30, 2005, abandoned, which is a continuation of U.S. application Ser. No. 10/456,986, filed Jun. 6, 2003, and issued as U.S. Pat. No. 7,064,107, which claims the benefit from U.S. Provisional Application No. 60/387,239, filed Jun. 7, 2002, and U.S. Provisional Application No. 60/407,003, filed Aug. 28, 2002.

The entire teachings of the above applications are incorporated herein by reference.

BACKGROUND OF THE INVENTION

Proteases are involved in a broad range of biological pathways. In particular, serine proteases such as kallikrein, plasmin, elastase, urokinase plasminogen activator, thrombin, human lipoprotein-associated coagulation inhibitor, and coagulation factors such as factors VIIa, IXa, Xa, XIa, and XIIa have been implicated in pathways affecting blood flow, e.g., general and focal ischemia, tumor invasion, fibrinolysis, perioperative blood loss, and inflammation. Inhibitors of specific serine proteases, therefore, have received attention as potential drug targets for various ischemic maladies.

One such inhibitor, aprotinin (also called bovine pancreatic trypsin inhibitor or BPTI), obtained from bovine lung, has been approved in the United States for prophylactic use in reducing perioperative blood loss and the need for transfusion in patients undergoing cardiopulmonary bypass (CPB), e.g., in the course of a coronary artery bypass grafting procedure. Aprotinin is commercially available under the trade name TRASYLOL®. (Bayer Corporation Pharmaceutical Division, West Haven, Conn.) and was previously approved for use to treat pancreatitis. The effectiveness of aprotinin is associated with its relatively non-specific abilities to inhibit a variety of serine proteases, including plasma kallikrein and plasmin. These proteases are important in a number of pathways of the contact activation system (CAS).

CAS is initially activated when whole blood contacts the surface of foreign substrates (e.g., kaolin, glass, dextran sulfate, or damaged bone surfaces). Kallikrein, a serine protease, is a plasma enzyme that initiates the CAS cascade leading to activation of neutrophils, plasmin, coagulation, and various kinins. Kallikrein is secreted as a zymogen (pre-kallikrein) that circulates as an inactive molecule until activated by a proteolytic event early in the contact activation cascade. Clearly, specific inhibition of kallikrein would be a very attractive approach to control blood loss associated with CPB and the onset of systemic inflammatory response (SIR) as would be encountered during, for example, various invasive surgical procedures.

Despite being the only licensed compound for preventing perioperative blood loss in CPB for coronary artery bypass grafting (CABG) procedures, aprotinin is not as widely used as would be expected. There are serious concerns regarding the use of this bovine polypeptide in patients who require CPB, and in particular the use of this compound in CABG procedures. Aprotinin is not specific for kallikrein, but interacts with additional enzymes (e.g., plasmin) in multiple pathways. Thus, the mechanism of action of aprotinin is largely speculative, and the lack of precise understanding of what is affected during aprotinin treatment produces the risk of complications during treatment. One frequently cited complication is uncontrolled thrombosis, due to aprotinin's actions upon the fibrinolytic pathway. There is concern not only over such hyperacute events as major vessel thrombosis in the perioperative period, but also over graft patency alter the CABG procedure. Furthermore, as a naturally occurring protein obtained from bovine lung, administration of aprotinin in humans can elicit severe hypersensitivity or anaphylactic or anaphylactoid reactions after the first and, more often, after repeat administration to patients. This is particularly of concern in the large number of patients who have repeat CABG procedures. In addition, there is an increasing public concern regarding use of material derived from bovine sources as a potential vector for the transmission of bovine spongiform encephalopathy to humans.

These concerns make clear that a need remains for more effective and more specific means and methods for preventing or reducing perioperative blood loss and the onset of SIR in a patient subjected to surgery resulting in activation of the CAS, such as CABG procedures in patients of CPB, or hip replacement.

SUMMARY OF THE INVENTION

This invention is based on the discovery of peptides that inhibit serine proteases. Serine proteases such as, for example, kallikrein, are involved in, for example, pathways leading to excessive perioperative blood loss and the onset of systemic inflammatory response. Preferred kallikrein peptide inhibitors include those described in U.S. Pat. Nos. 6,333,402 and 6,057,287 to Markland et al., the contents of which are incorporated herein by reference in their entirety. The invention is directed in part to the use of the peptides in therapeutic methods and compositions suitable for use in eliminating or reducing various ischemias, including but not limited to perioperative blood loss, and the onset of systemic inflammatory response. Perioperative blood loss results from invasive surgical procedures that lead to contact activation of complement components and the coagulation/fibrinolysis systems. More specifically, the invention provides methods of using kallikrein inhibitors to reduce or prevent perioperative blood loss and a systemic inflammatory response in patients subjected to invasive surgical procedures, especially cardiothoracic surgeries.

In one embodiment, the invention is directed to a method for preventing or reducing ischemia in a patient comprising administering to the patient a composition comprising a polypeptide comprising the amino acid sequence: Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO:1), wherein Xaa1, Xaa2, Xaa3, Xaa4, Xaa56, Xaa57 or Xaa58 are each individually an amino acid or absent; Xaa10 is an amino acid selected from the group consisting of: Asp and Glu; Xaa11 is an amino acid selected from the group consisting of: Asp, Gly, Ser, Val, Asn, Ile, Ala and Thr; Xaa13 is an amino acid selected from the group consisting of: Arg, His, Pro, Asn, Ser, Thr, Ala, Gly, Lys and Gln; Xaa15 is an amino acid selected from the group consisting of: Arg, Lys, Ala, Ser, Gly, Met, Asn and Gln; Xaa16 is an amino acid selected from the group consisting of: Ala, Gly, Ser, Asp and Asn; Xaa17 is an amino acid selected from the group consisting of: Ala, Asn, Ser, Ile, Gly, Val, Gln and Thr; Xaa18 is an amino acid selected from the group consisting of:

His, Leu, Gln and Ala; Xaa19 is an amino acid selected from the group consisting of: Pro, Gln, Leu, Asn and Ile; Xaa21 is an amino acid selected from the group consisting of: Trp, Phe, Tyr, His and Ile; Xaa22 is an amino acid selected from the group consisting of: Tyr and Phe; Xaa23 is an amino acid selected from the group consisting of: Tyr and Phe; Xaa31 is an amino acid selected from the group consisting of: Glu, Asp, Gln, Asn, Ser, Ala, Val, Leu, Ile and Thr; Xaa32 is an amino acid selected from the group consisting of: Glu, Gln, Asp Asn, Pro, Thr, Leu, Ser, Ala, Gly and Val; Xaa34 is an amino acid selected from the group consisting of: Thr, Ile, Ser, Val, Ala, Asn, Gly and Leu; Xaa35 is an amino acid selected from the group consisting of: Tyr, Trp and Phe; Xaa39 is an amino acid selected from the group consisting of: Glu, Gly, Ala, Ser and Asp; Xaa40 is an amino acid selected from the group consisting of Gly and Ala; Xaa43 is an amino acid selected from the group consisting of: Asn and Gly; Xaa45 is an amino acid selected from the group consisting of: Phe and Tyr; and wherein the polypeptide inhibits kallikrein.

In a particular embodiment, the ischemia is perioperative blood loss due to a surgical procedure performed on the patient. The surgical procedure can be a cardiothoracic surgery, such as, for example, cardiopulmonary bypass or coronary artery bypass grafting.

In a particular embodiment, individual amino acid positions of SEQ ID NO:1 can be one or more of the following: Xaa10 is Asp, Xaa11 is Asp, Xaa13 is Pro, Xaa15 is Arg, Xaa16 is Ala, Xaa17 is Ala, Xaa18 is His, Xaa19 is Pro, Xaa21 is Trp, Xaa31 is Glu, Xaa32 is Glu, Xaa34 is Ile, Xaa35 is Tyr, Xaa39 is Glu.

In another embodiment, the invention is directed to a method for preventing or reducing the onset of systemic inflammatory response associated with a surgical procedure in a patient comprising administering to the patient a composition comprising a polypeptide comprising the amino acid sequence: Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO:1), wherein Xaa1, Xaa2, Xaa3, Xaa4, Xaa56, Xaa57 or Xaa58 are each individually an amino acid or absent; Xaa10 is an amino acid selected from the group consisting of: Asp and Glu; Xaa11 is an amino acid selected from the group consisting of: Asp, Gly, Ser, Val, Asn, Ile, Ala and Thr; Xaa13 is an amino acid selected from the group consisting of Arg, His, Pro, Asn, Ser, Thr, Ala, Gly, Lys and Gln; Xaa15 is an amino acid selected from the group consisting of: Arg, Lys, Ala, Ser, Gly, Met, Asn and Gln; Xaa16 is an amino acid selected from the group consisting of: Ala, Gly, Ser, Asp and Asn; Xaa17 is an amino acid selected from the group consisting of: Ala, Asn, Ser, Ile, Gly, Val, Gln and Thr; Xaa18 is an amino acid selected from the group consisting of: His, Leu, Gln and Ala; Xaa19 is an amino acid selected from the group consisting of Pro, Gln, Leu, Asn and Ile; Xaa21 is an amino acid selected from the group consisting of: Trp, Phe, Tyr, His and Ile; Xaa22 is an amino acid selected from the group consisting of: Tyr and Phe; Xaa23 is an amino acid selected from the group consisting of: Tyr and Phe; Xaa31 is an amino acid selected from the group consisting of: Glu, Asp, Gln, Asn, Ser, Ala, Val, Leu, Ile and Thr; Xaa32 is an amino acid selected from the group consisting of: Glu, Gln, Asp Asn, Pro, Thr, Leu, Ser, Ala, Gly and Val; Xaa34 is an amino acid selected from the group consisting of: Thr, Ile, Ser, Val, Ala, Asn, Gly and Leu; Xaa35 is an amino acid selected from the group consisting of: Tyr, Trp and Phe; Xaa39 is an amino acid selected from the group consisting of: Glu, Gly, Ala, Ser and Asp; Xaa40 is an amino acid selected from the group consisting of: Gly and Ala; Xaa43 is an amino acid selected from the group consisting of: Asn and Gly; Xaa45 is an amino acid selected from the group consisting of: Phe and Tyr; and wherein the polypeptide inhibits kallikrein. In a particular embodiment, the surgical procedure can be a cardiothoracic surgery, such as, for example, cardiopulmonary bypass or coronary artery bypass grafting. In a particular embodiment, individual amino acid positions of SEQ ID NO:1 can be one or more of the following: Xaa10 is Asp, Xaa11 is Asp, Xaa13 is Pro, Xaa15 is Arg, Xaa16 is Ala, Xaa17 is Ala, Xaa18 is His, Xaa19 is Pro, Xaa21 is Trp, Xaa31 is Glu, Xaa32 is Glu, Xaa34 is Ile, Xaa35 is Tyr, Xaa39 is Glu.

In yet another embodiment, the invention is directed to a method for preventing or reducing the onset of systemic inflammatory response associated with a surgical procedure in a patient comprising administering to the patient a composition comprising a polypeptide consisting of the amino acid sequence: Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:2), wherein the polypeptide inhibits kallikrein. In one embodiment, the surgical procedure is a cardiothoracic surgery, such as, for example, cardiopulmonary bypass or coronary artery bypass grafting.

In another embodiment, the invention is directed to a method for preventing or reducing ischemia in a patient comprising administering to the patient a composition comprising a polypeptide consisting of the amino acid sequence: Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:2), wherein the polypeptide inhibits; kallikrein. In a particular embodiment, the ischemia can be perioperative blood loss due to a surgical procedure performed on the patient. In one embodiment, the surgical procedure is a cardiothoracic surgery, such as, for example, cardiopulmonary bypass or coronary artery bypass grafting.

In yet another embodiment, the invention is directed to a method for preventing or reducing the onset of systemic inflammatory response associated with a surgical procedure in a patient comprising administering to the patient a composition comprising a polypeptide consisting of the amino acid sequence: Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (amino acids 3-60 of SEQ ID NO:2), wherein the polypeptide inhibits kallikrein. In one embodiment, the surgical procedure is a cardiothoracic surgery, such as, for example, cardiopulmonary bypass or coronary artery bypass grafting.

In another embodiment, the invention is directed to a method for preventing or reducing ischemia in a patient comprising administering to the patient a composition comprising a polypeptide consisting of the amino acid sequence: Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (amino acids 3-60 of SEQ ID NO:2), wherein the polypeptide inhibits kallikrein. In a particular embodiment, the ischemia can be perioperative blood loss due to a surgical procedure performed on the patient. In one embodiment, the surgical procedure is a cardiothoracic surgery, such as, for example, cardiopulmonary bypass or coronary artery bypass grafting.

BRIEF DESCRIPTION OF THE DRAWINGS

FIG. 2 shows a portion of a DNA and corresponding deduced amino acid for a KI polypeptide of the invention in plasmid pPIC-K503. The inserted DNA encodes the mat.alpha. prepro signal peptide of *Saccharomyces cerevisiae* (underlined) fused in frame to the amino terminus of the PEP-1 KI polypeptide having the amino acid sequence enclosed by the boxed area. The amino acid sequence of the PEP-1 KI polypeptide shown in the boxed region is SEQ ID NO:2, and the corresponding nucleotide coding sequence of the KI polypeptide is SEQ ID NO:3. The dashed arrows indicate the location and direction of two PCR primer sequences in AOX regions that were used to produce sequencing templates. DNA sequence for the entire nucleotide sequence of the figure comprises the structural coding sequence for the fusion protein and is designated SEQ ID NO:27. The entire amino acid sequence is SEQ ID NO:28. The double underlined portion of the sequence indicates a diagnostic probe sequence. BstBI and EcoRI indicate locations of their respective palindromic, hexameric, restriction endonuclease sites in the sequence. Asterisks denote translational stop codons.

FIGS. 3A and 3B show an alignment of amino acid sequences of the preferred embodiments of the invention, the native LACI sequence from which these variants were derived (SEQ ID NO:32), and other known Kunitz domains (SEQ ID NOS:29-31 and 33-53). Cysteine residues are highlighted.

DETAILED DESCRIPTION OF THE INVENTION

Figure 1:
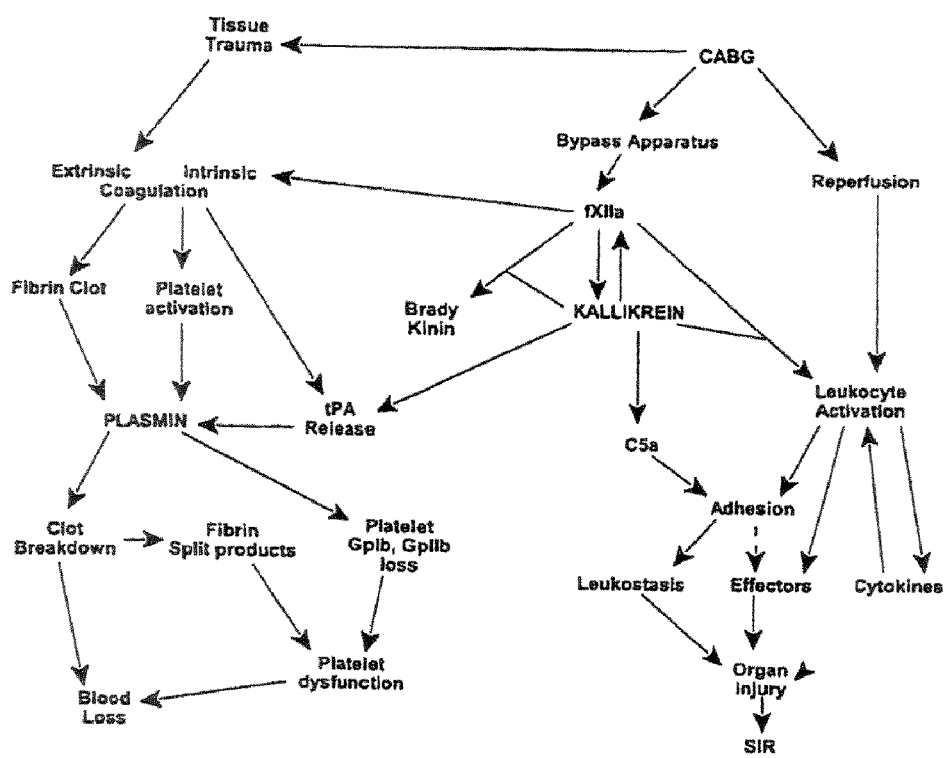
FIG. 1 is a simplified diagram of major multiple pathways and related events involved in the contact activation system and systemic inflammatory response (SIR) that can arise in a patient subjected to soft and bone tissue trauma such as that associated with a coronary artery bypass grafting (CABG) procedure, especially when the CABG procedure involves extra-corporeal blood circulation, such as cardiopulmonary bypass (Bypass Apparatus). Arrows indicate activation from one component or event to another component or event in the cascade. Arrows in both directions indicate activating effects of components or events in both directions. Broken arrows indicate likely participation of one component or event in the activation of another component or event. Abbreviations are as follows: "tPA"=tissue plasminogen activator; "C5a"=a protein component of the complement system; "fXIIa"=activator protein of prekallikrein to form active kallikrein; "Extrinsic"=extrinsic coagulation system; "Intrinsic"=intrinsic coagulation system.

A description of preferred embodiments of the invention follows.

The invention is based on the discovery of a group of kallikrein inhibitor (KI) polypeptides that inhibit plasma kallikrein with a specificity that permits their use in improved methods of preventing or reducing ischemia such as, for example, perioperative blood loss and/or a systemic inflammatory response (SIR) induced by kallikrein, especially, for example, in patients undergoing surgical procedures and particularly surgical procedures involving cardiothoracic surgery, e.g., cardiopulmonary bypass (CPB), such as a coronary artery bypass graft (CABG) procedures. K's can be used specifically for, e.g., pediatric cardiac surgery, lung transplantation, total hip replacement and orthotopic liver transplantation, and to reduce or prevent perioperative stroke during CABG, extracorporeal membrane oxygenation (ECMO) and cerebrovascular accidents (CVA) during these procedures.

Cardiothoracic surgery is surgery of the chest area, most commonly the heart and lungs. Typical diseases treated by cardiothoracic surgery include coronary artery disease, tumors and cancers of the lung, esophagus and chest wall, heart vessel and valve abnormalities, and birth defects involving the chest or heart. Where cardiothoracic surgery is utilized for treatment, the risk of blood loss (e.g., surgery-induced ischemia) and the onset of a systemic inflammatory response (SIR) is incurred. Surgery-induced SIR can result in severe organ dysfunction (systemic inflammatory response syndrome; SIRS).

Polypeptides Useful in the Invention

KI polypeptides useful in the invention comprise Kunitz domain polypeptides. In one embodiment these Kunitz domains are variant forms of the looped structure comprising Kunitz domain I of human lipoprotein-associated coagulation inhibitor (LACI) protein. LACI contains three internal, well-defined, peptide loop structures that are paradigm Kunitz domains (Girard, T. et al., 1989. Nature, 338:518-520). The three Kunitz domains of LACI confer the ability to bind and inhibit kallikrein, although not with exceptional affinity. Variants of Kunitz domain 1 of LACI described herein have been screened, isolated and bind kallikrein with enhanced affinity and specificity (see, for example, U.S. Pat. Nos. 5,795,865 and 6,057,287, incorporated herein by reference). An example of a preferred polypeptide useful in the invention has the amino acid sequence defined by amino acids 3-60 of SEQ ID NO:2.

Every polypeptide useful in the invention binds kallikrein, and preferred polypeptides are also kallikrein inhibitors (KI) as determined using kallikrein binding and inhibition assays known in the art. The enhanced affinity and specificity for kallikrein of the variant Kunitz domain polypeptides described herein provides the basis for their use in cardiothoracic surgery, e.g., CPB and especially CABG surgical procedures, to prevent or reduce perioperative blood loss and/or the onset of SIR in patients undergoing such procedures. The KI polypeptides used in the invention have or comprise the amino acid sequence of a variant Kunitz domain polypeptide originally isolated by screening phage display libraries for the ability to bind kallikrein.

KI polypeptides useful in the methods and compositions of the invention comprise a Kunitz domain polypeptide comprising the amino acid sequence:

```
                                          (SEQ ID NO: 1)
Xaa1 Xaa2 Xaa3 Xaa4 Cys Xaa6 Xaa7 Xaa8 Xaa9 Xaa10

Xaa11 Gly Xaa13 Cys Xaa15 Xaa16 Xaa17 Xaa18 Xaa19

Xaa20 Xaa21 Xaa22 Xaa23 Xaa24 Xaa25 Xaa26 Xaa27

Xaa28 Xaa29 Cys Xaa31 Xaa32 Phe Xaa34 Xaa35 Gly

Gly Cys Xaa39 Xaa40 Xaa41 Xaa42 Xaa43 Xaa44 Xaa45

Xaa46 Xaa47 Xaa48 Xaa49 Xaa50 Cys Xaa52 Xaa53

Xaa54 Cys Xaa56 Xaa57 Xaa58
```

"Xaa" refers to a position in a peptide chain that can be any of a number of different amino acids. For example, for the KI peptides described herein, Xaa10 can be Asp or Glu; Xaa11 can be Asp, Gly, Ser, Val, Asn, Ile, Ala or Thr; Xaa13 can be Pro, Arg, His, Asn, Ser, Thr, Ala, Gly, Lys or Gln; Xaa15 can be Arg, Lys, Ala, Ser, Gly, Met, Asn or Gln; Xaa16 can be Ala, Gly, Ser, Asp or Asn; Xaa17 can be Ala, Asn, Ser, Ile, Gly, Val, Gln or Thr; Xaa18 can be His, Leu, Gln or Ala; Xaa19 can be Pro, Gln, Leu, Asn or Ile; Xaa21 can be Trp, Phe, Tyr, His or Ile; Xaa31 can be Glu, Asp, Gln, Asn, Ser, Ala, Val, Leu, Ile or Thr; Xaa32 can be Glu, Gln, Asp Asn, Pro, Thr, Leu, Ser, Ala, Gly or Val; Xaa34 can be Ile, Thr, Ser, Val, Ala, Asn, Gly or Leu; Xaa35 can be Tyr, Trp or Phe; Xaa39 can be Glu, Gly, Ala, Ser or Asp. Amino acids Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 can be any amino acid. Additionally, each or the first four and at last three amino acids of SEQ ID NO:1 can optionally be present or absent and can be any amino acid, if present.

Peptides defined according to SEQ ID NO:1 form a set of polypeptides that bind to kallikrein. For example, in a preferred embodiment of the invention, a KI polypeptide useful in the methods and compositions of the invention has the following variable positions: Xaa11 can be Asp, Gly, Ser or Val; Xaa13 can be Pro, Arg, His or Asn; Xaa15 can be Arg or Lys; Xaa16 can be Ala or Gly; Xaa17 can be Ala, Asn, Ser or Ile; Xaa18 can be His, Leu or Gln; Xaa19 can be Pro, Gln or Leu; Xaa21 can be Trp or Phe; Xaa31 is Glu; Xaa32 can be Glu or Gln; Xaa34 can be Ile, Thr or Ser; Xaa35 is Tyr; and Xaa39 can be Glu, Gly or Ala.

A more specific embodiment of the claimed invention is defined by the following amino acids at variable positions: Xaa10 is Asp; Xaa11 is Asp; Xaa13 can be Pro or Arg; Xaa15 is Arg; Xaa16 can be Ala or Gly; Xaa17 is Ala; Xaa18 is His; Xaa19 is Pro; Xaa21 is Trp; Xaa31 is Glu; Xaa32 is Glu; Xaa34 can be Ile or Ser; Xaa35 is Tyr; and Xaa39 is Gly.

Also encompassed within the scope of the invention are peptides that comprise portions of the polypeptides described herein. For example, polypeptides could comprise binding domains for specific kallikrein epitopes. Such fragments of the polypeptides described herein would also be encompassed.

KI polypeptides useful in the methods and compositions described herein comprise a Kunitz domain. A subset of the sequences encompassed by SEQ ID NO:1 are described by the following (where not indicated, "Xaa" refers to the same set of amino acids that are allowed for SEQ ID NO: 1):

```
                                         (SEQ ID NO: 54)
Met His Ser Phe Cys Ala Phe Lys Ala Xaa10 Xaa11

Gly Xaa13 Cys Xaa15 Xaa16 Xaa17 Xaa18 Xaa19 Arg

Xaa21 Phe Phe Asn Ile Phe Thr Arg Gln Cys Xaa31

Xaa32 Phe Xaa34 Xaa35 Gly Gly Cys Xaa39 Gly Asn

Gln Asn Arg Phe Glu Ser Leu Glu Glu Cys Lys Lys

Met Cys Thr Arg Asp.

(amino acids 3-60 of SEQ ID NO: 2)
Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp, (SEQ ID NO: 4)
Met His Ser Phe Cys Ala Phe Lys Ala Asp Asp Gly Pro Cys Lys Ala Asn His Leu Arg Phe Phe Asn Ile Phe Thr Arg Gln Cys Gln Gln Phe Ser Tyr Gly Gly Cys Gly Gly Asn Gln Asn Arg Phe Glu Ser Leu Glu Glu Cys Lys Lys Met Cys Thr Arg Asp, (SEQ ID NO: 5)
Met His Ser Phe Cys Ala Phe Lys Ala Asp Asp Gly His Cys Lys Ala Asn His Gln Arg Phe Phe Asn Ile Phe Thr Arg Gln Cys Glu Glu Phe Thr Tyr Gly Gly Cys Gly Gly Asn Gln Asn Arg Phe Glu Ser Leu Glu Glu Cys Lys Lys Met Cys Thr Arg Asp, (SEQ ID NO: 6)
Met His Ser Phe Cys Ala Phe Lys Ala Asp Asp Gly His Cys Lys Ala Asn His Gln Arg Phe Phe Asn Ile Phe Thr Arg Gln Cys Glu Gln Phe Thr Tyr Gly Gly Cys Ala Gly Asn Gln Asn Arg Phe Glu Ser Leu Glu Glu Cys Lys Lys Met Cys Thr Arg Asp, (SEQ ID NO: 7)
His Cys Lys Ala Ser Leu Pro Arg Phe Phe Phe Asn Ile Phe Thr Arg Gln Cys Glu Glu Phe Ile Tyr Gly Gly Cys Gly Gly Asn Gln Asn Arg Phe Glu Ser Leu Glu Glu Cys Lys Lys Met Cys Thr Arg Asp, (SEQ ID NO: 8)
Met His Ser Phe Cys Ala Phe Lys Ala Asp Asp Gly His Cys Lys Ala Asn His Gln Arg Phe Phe Asn Ile Phe Thr Arg Gln Cys Glu Glu Phe Ser Tyr Gly Gly Cys Gly Gly Asn Gln Asn Arg Phe Glu Ser Leu Glu Glu Cys Lys Lys Met Cys Thr Arg Asp, (SEQ ID NO: 9)
Met His Ser Phe Cys Ala Phe Lys Ala Asp Asp Gly His Cys Lys Gly Ala His Leu Arg Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp, (SEQ ID NO: 10)
Met His Ser Phe Cys Ala Phe Lys Ala Asp Asp Gly Arg Cys Lys Gly Ala His Leu Arg Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp, (SEQ ID NO: 11)
Met His Ser Phe Cys Ala Phe Lys Ala Asp Gly Gly Arg Cys Arg Gly Ala His Pro Arg Trp Phe Phe Asn
```

```
Ile Phe Thr Arg Gln Cys Glu Glu Phe Ser Tyr Gly

Gly Cys Gly Gly Asn Gln Asn Arg Phe Gln Ser Leu

Glu Glu Cys Lys Lys Met Cys Thr Arg Asp,
                                            (SEQ ID NO: 12)
Met His Ser Phe Cys Ala Phe Lys Ala Asp Asp Gly

Pro Cys Arg Ala Ala His Pro Arg Trp Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp,
                                            (SEQ ID NO: 13)
Met His Ser Phe Cys Ala Phe Lys Ala Asp Val Gly

Arg Cys Arg Gly Ala His Pro Arg Trp Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp,
                                            (SEQ ID NO: 14)
Met His Ser Phe Cys Ala Phe Lys Ala Asp Val Gly

Arg Cys Arg Gly Ala Gln Pro Arg Phe Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp,
                                            (SEQ ID NO: 15)
Met His Ser Phe Cys Ala Phe Lys Ala Asp Asp Gly

Ser Cys Arg Ala Ala His Leu Arg Trp Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp,
                                            (SEQ ID NO: 16)
Met His Ser Phe Cys Ala Phe Lys Ala Glu Gly Gly

Ser Cys Arg Ala Ala His Gln Arg Trp Phe Phe Asn

Phe Thr Arg Gln Cys Glu Glu Phe Ser Tyr Gly Gly

Cys Gly Gly Asn Gln Asn Arg Phe Glu Ser Leu Glu

Glu Cys Lys Lys Met Cys Thr Arg Asp,
                                            (SEQ ID NO: 17)
Met His Ser Phe Cys Ala Phe Lys Ala Asp Asp Gly

Pro Cys Arg Gly Ala His Leu Arg Phe Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp,
                                            (SEQ ID NO: 18)
Met His Ser Phe Cys Ala Phe Lys Ala Asp Asp Gly

His Cys Arg Gly Ala Leu Pro Arg Trp Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp,
                                            (SEQ ID NO: 19)
Met His Ser Phe Cys Ala Phe Lys Ala Asp Ser Gly

Asn Cys Arg Gly Asn Leu Pro Arg Phe Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp,
                                            (SEQ ID NO: 20)
Met His Ser Phe Cys Ala Phe Lys Ala Asp Ser Gly

Arg Cys Arg Gly Asn His Gln Arg Phe Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp,
                                            (SEQ ID NO: 21)
Met His Ser Phe Cys Ala Phe Lys Ala Asp Gly Gly

Arg Cys Arg Ala Ile Gln Pro Arg Trp Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp,
                                            (SEQ ID NO: 22)
Met His Ser Phe Cys Ala Phe Lys Ala Asp Asp Gly

Arg Cys Arg Gly Ala His Pro Arg Trp Phe Phe Asn

Ile Phe Thr Arg Gln Cys Glu Glu Phe Ser Tyr Gly

Gly Cys Gly Gly Asn Gln Asn Arg Phe Glu Ser Leu

Glu Glu Cys Lys Lys Met Cys Thr Arg Asp.
```

FIGS. 3A and 3B provides an amino acid sequence alignment of these sequences, the native LACI sequence from which these variants were derived (SEQ ID NO:32), and other known Kunitz domains (SEQ ID NOS: 29-31 and 33-53).

The KI polypeptides useful in the methods and compositions described herein can be made synthetically using any standard polypeptide synthesis protocol and equipment. For example, the stepwise synthesis of a KI polypeptide described herein can be carried out by the removal of an amino (N) terminal-protecting group from an initial (i.e., carboxy-terminal) amino acid, and coupling thereto of the carboxyl end of the next amino acid in the sequence of the polypeptide. This amino acid is also suitably protected. The carboxyl group of the incoming amino acid can be activated to react with the N-terminus of the bound amino acid by formation into a reactive group such as formation into a carbodiimide, a symmetric acid anhydride, or an "active ester" group such as hydroxybenzotriazole or pentafluorophenyl esters. Preferred solid-phase peptide synthesis methods include the BOC method, which utilizes tert-butyloxycarbonyl as the .alpha.-amino protecting group, and the FMOC method, which utilizes 9-fluorenylmethloxycarbonyl to protect the .alpha.-amino of the amino acid residues. Both methods are well known to those of skill in the art (Stewart, J. and Young, J., Solid-Phase Peptide Synthesis (W.H. Freeman Co., San Francisco 1989); Merrifield, J., 1963. Am. Chem. Soc., 85:2149-2154; Bodanszky, M. and Bodanszky, A., The Practice of Peptide Synthesis (Springer-Verlag, New York 1984), the entire teachings of these references is incorporated herein by reference). If desired, additional amino- and/or carboxy-terminal amino acids can be designed into the amino acid sequence and added during polypeptide synthesis.

Alternatively, Kunitz domain polypeptides and KI polypeptides useful in the compositions and methods of the invention can be produced by recombinant methods using any of a number of cells and corresponding expression vectors, including but not limited to bacterial expression vectors, yeast expression vectors, baculovirus expression vectors, mammalian viral expression vectors, and the like. Kunitz domain polypeptides and KI polypeptides useful in the compositions and methods of the invention can also be produced transgenically using nucleic acid molecules comprising a coding sequence for a Kunitz domain or KI polypeptide described herein, wherein the nucleic acid molecule can be integrated into and expressed from the genome of a host animal using transgenic methods available in the art. In some cases, it could be necessary or advantageous to fuse the coding sequence for a Kunitz domain polypeptide or a KI polypeptide comprising the Kunitz domain to another coding sequence in an expression vector to form a fusion polypeptide that is readily expressed in a host cell. Preferably, the host cell that expresses such a fusion polypeptide also processes the fusion polypeptide to yield a Kunitz domain or KI polypeptide useful in the invention that contains only the desired amino acid sequence. Obviously, if any other amino acid(s) remain attached to the expressed Kunitz domain or KI polypeptide, such additional amino acid(s) should not diminish the kallikrein binding and/or kallikrein inhibitory activity of the Kunitz domain or KI polypeptide so as to preclude use of the polypeptide in the methods or compositions of the invention.

A preferred recombinant expression system for producing KI polypeptides useful in the methods and compositions described herein is a yeast expression vector, which permits a nucleic acid sequence encoding the amino acid sequence for a KI polypeptide or Kunitz domain polypeptide to be linked in the same reading frame with a nucleotide sequence encoding the mat.alpha. prepro leader peptide sequence of *Saccharomyces cerevisiae*, which in turn is under the control of an operable yeast promoter. The resulting recombinant yeast expression plasmid can then be transformed by standard methods into the cells of an appropriate, compatible yeast host, which cells are able to express the recombinant protein from the recombinant yeast expression vector. Preferably, a host yeast cell transformed with such a recombinant expression vector is also able to process the fusion protein to provide an active KI polypeptide useful in the methods and compositions of the invention. A preferred yeast host for producing recombinant Kunitz domain polypeptides and KI polypeptides comprising such Kunitz domains is *Pichia pastoris*.

As noted above, KI polypeptides that are useful in the methods and compositions described herein can comprise a Kunitz domain polypeptide described herein. Some KI polypeptides can comprise an additional flanking sequence, preferably of one to six amino acids in length, at the amino and/or carboxy-terminal end, provided such additional amino acids do not significantly diminish kallikrein binding affinity or kallikrein inhibition activity so as to preclude use in the methods and compositions described herein. Such additional amino acids can be deliberately added to express a KI polypeptide in a particular recombinant host cell or can be added to provide an additional function, e.g., to provide a peptide to link the KI polypeptide to another molecule or to provide an affinity moiety that facilitates purification of the polypeptide. Preferably, the additional amino acid(s) do not include cysteine, which could interfere with the disulfide bonds of the Kunitz domain.

An example of a preferred Kunitz domain polypeptide useful in the methods and compositions of the invention has the amino acid sequence of residues 3-60 of SEQ ID NO:2. When expressed and processed in a yeast fusion protein expression system (e.g., based on the integrating expression plasmid pHIL-D2), such a Kunitz domain polypeptide retains an additional amino terminal Glu-Ala dipeptide from the fusion with the mat.alpha. prepro leader peptide sequence of *S. cerevisiae*. When secreted from the yeast host cell, most of the leader peptide is processed from the fusion protein to yield a functional KI polypeptide (referred to herein as "PEP-1") having the amino acid sequence of SEQ ID NO:2 (see boxed region in FIG. 2).

Particularly preferred KI polypeptides useful in the methods and compositions described herein have a binding affinity for kallikrein that is on the order of 1000 times higher than that of aprotinin, which is currently approved for use in CABG procedures to reduce blood loss. The surprisingly high binding affinities of such KI polypeptides described herein indicate that such KI polypeptides exhibit a high degree of specificity for kallikrein to the exclusion or other molecular targets (see Table 1, below). Thus, use of such polypeptides according to the invention reduces much of the speculation as to the possible therapeutic targets in a patient. The lower degree of specificity exhibited by, for example, aprotinin, leads to possible pleiotropic side effects and ambiguity as to its therapeutic mechanism.

The polypeptides defined by, for example, SEQ ID NO:1 contain invariant positions, e.g., positions 5, 14, 30, 51 and 55 can be Cys only. Other positions such as, for example, positions 6, 7, 8, 9, 20, 24, 25, 26, 27, 28, 29, 41, 42, 44, 46, 47, 48, 49, 50, 52, 53 and 54 can be any amino acid (including non-naturally occurring amino acids). In a particularly preferred embodiment, one or more amino acids correspond to that of a native sequence (e.g., SEQ ID NO:32, see FIG. 3). In a preferred embodiment, at least one variable position is different from that of the native sequence. In yet another preferred embodiment, the amino acids can each be individually or collectively substituted by a conservative or non-conservative amino acid substitution. Conservative amino acid substitutions replace an amino acid with another amino acid of similar chemical structure and may have no affect on protein function. Non-conservative amino acid substitutions replace an amino acid with another amino acid of dissimilar chemical structure. Examples of conserved amino acid substitutions include, for example, Asn->Asp, Arg->Lys and Ser->Thr. In a preferred embodiment, 1, 2, 3, 4, 5, 6, 7, 8, 9, 10, 11, 12, 13, 14, 15, 16, 17, 18, 19, 20 and/or 21 of these amino acids can be independently or collectively, in any combination, selected to correspond to the corresponding position of SEQ ID NO:2.

Other positions, for example, positions 10, 11, 13, 15, 16, 17, 18, 19, 21, 22, 23, 31, 32, 34, 35, 39, 40, 43 and 45, can be any of a selected set of amino acids. Thus SEQ ID NO:1 defines a set of possible sequences. Each member of this set contains, for example, a cysteine at positions 5, 14, 30, 51 and 55, and any one of a specific set of amino acids at positions 10, 11, 13, 15, 16, 17, 18, 19, 221, 22, 23, 31, 32, 34, 35, 39, 40, 43 and 45. In a preferred embodiment, 1, 2, 3, 4, 5, 6, 7, 8, 9, 10, 11, 12, 13, 14, 15, 16, 17, 18 and/or 19 of these amino acids can be independently or collectively, in any combination, selected to correspond to the corresponding position of SEQ ID NO:2. The peptide preferably has at least 80%, at least 85%, at least 90% or at least 95% identity to SEQ ID NO:2.

Methods and Compositions

The present invention is also directed to methods for preventing or reducing ischemia. Preferred in the invention are methods for preventing or reducing perioperative blood loss and/or a systemic inflammatory response (SIR) in a patient, especially associated with cardiothoracic surgery. A method for treatment involves the administration of a KI polypeptide comprising a Kunitz domain. One embodiment of the method involves using a peptide containing an amino acid sequence of SEQ ID NO:1 that has an affinity for kallikrein that is approximately 1000-fold or more higher than that of a broad range serine protease, e.g., aprotinin, which is isolated from bovine lung and currently approved for use in CABG procedures (TRASYLOL®, Bayer Corporation Pharmaceutical Division, West Haven, Conn.).

Patients subjected to any of a number of surgical procedures, especially those involving extra-corporeal circulation, e.g., cardiothoracic surgery, such as, for example, CPB, and/or bone trauma, such as sternal split or hip replacement, are at risk for perioperative blood loss and inflammation. Contact of a patient's blood with the cut surfaces of bone or of CPB equipment is sufficient to activate one or several undesirable cascade responses, including a contact activation system (CAS), which can lead to extensive perioperative blood loss requiring immediate blood transfusion, as well as a systemic inflammatory response (SIR), which, in turn, can result in permanent damage to tissues and organs. While not desiring to be limited to any particular mechanism or theory, it appears that the blood loss that occurs associated with cardiothoracic surgery, e.g., CPB, as in a CABG procedure, probably results from extensive capillary leakage, which can result in significant loss of blood that must be replaced by immediate blood transfusion.

The methods described herein are useful for preventing or reducing various ischemias including, for example, perioperative blood loss and SIR in a patient subjected to a surgical procedure, and especially wherein the surgical procedure requires extra-corporeal circulation, e.g., cardiothoracic surgery, such as, for example, CPB. The methods of the invention are particularly useful for preventing or reducing perioperative blood loss and/or SIR in a patient subjected to a CABG procedure requiring CPB or other cardiac surgery.

Preferred compositions for medical use comprise a KI polypeptide described herein. Such compositions useful can further comprise one or more pharmaceutically acceptable buffers, carriers, and excipients, which can provide a desirable feature to the composition including, but not limited to, enhanced administration of the composition to a patient, enhanced circulating half-life of the KI polypeptide of the composition, enhanced compatibility of the composition with patient blood chemistry, enhanced storage of the composition, and/or enhanced efficacy of the composition upon administration to a patient. In addition to a KI polypeptide described herein, compositions can further comprise one or more other pharmaceutically active compounds that provide an additional prophylactic or therapeutic benefit to a patient of an invasive surgical procedure.

Compositions useful in the methods of the invention comprise any of the Kunitz domain polypeptides or KI polypeptides comprising such Kunitz domain polypeptides described herein. Particularly preferred are KI polypeptides comprising a Kunitz domain polypeptide having a 58-amino acid sequence of amino acids 3-60 of SEQ ID NO:2. An example of such a particularly preferred KI polypeptide useful in the methods and compositions of the invention is the PEP-1 KI polypeptide having the 60-amino acid sequence of SEQ ID NO:2. A nucleotide sequence encoding the amino acid sequence of SEQ ID NO:2 is provided in SEQ ID NO:3 (see, e.g., nucleotides 309-488 in FIG. 2). It is understood that based on the known genetic code, the invention also provides degenerate forms of the nucleotide sequence of SEQ ID NO:3 by simply substituting one or more of the known degenerate codons for each amino acid encoded by the nucleotide sequence. Nucleotides 7-180 of SEQ ID NO:3, and degenerate forms thereof, encode the non-naturally occurring Kunitz domain polypeptide having the 58-amino acid sequence of amino acids 3-60 of SEQ ID NO:2.

Any of a variety of nucleic acid molecules can comprise the nucleotide sequence of nucleotides 7-180 of SEQ ID NO:3, degenerate forms, and portions thereof, including but not limited to, recombinant phage genomes, recombinant mammalian viral vectors, recombinant insect viral vectors, yeast mini chromosomes, and various plasmids. Such plasmids include those used to clone and/or express such nucleotide coding sequences. Expression vectors provide a promoter, which can be operably linked to a particular nucleotide sequence and an appropriate host cell, which is able to transcribe the particular nucleotide coding sequence into a functional messenger RNA (mRNA) and also translate the mRNA into the corresponding polypeptide. A polypeptide so produced can then be isolated from the host cell. Nucleic acid molecules comprising a nucleic acid sequence encoding a Kunitz domain or KI polypeptide described herein can be made by standard nucleic acid synthesis methods, recombinant DNA methodologies, polymerase chain reaction (PCR) methods, and any combination thereof.

Perioperative Blood Loss and Reduced Heart Bloodflow

Due to the many advances in medicine, a number of highly invasive surgical procedures are carried out each day that result in blood loss, or place patients at a high risk for blood loss. Such patients must be carefully monitored to restore and maintain normal blood supply and hemostasis, and they may need blood transfusions. Surgical procedures that involve blood loss include those involving extra-corporeal circulation methods such as cardiothoracic surgery, e.g., CPB. In such methods, a patient's heart is stopped and the circulation, oxygenation, and maintenance of blood volume are carried out artificially using an extra-corporeal circuit and a synthetic membrane oxygenator. These techniques are commonly used during cardiac surgery. Additionally, it is apparent that surgery involving extensive trauma to bone, such as the sternal split necessary in CABG or hip replacement procedures, is also associated with activation of the CAS, which can result in a variety of disruptions in the blood and vasculature.

Atherosclerotic coronary artery disease (CAD) causes a narrowing of the lumen of one or several of the coronary arteries; this limits the flow of blood to the myocardium (i.e., the heart muscle) and can cause angina, heart failure, and myocardial infarcts. In the end stage of coronary artery atherosclerosis, the coronary circulation can be almost completely occluded, causing life threatening angina or heart failure, with a very high mortality. CABG procedures may be required to bridge the occluded blood vessel and restore blood to the heart; these are potentially life saving. CABG procedures are among the most invasive of surgeries in which one or more healthy veins or arteries are implanted to provide a "bypass" around the occluded area of the diseased vessel. CABG procedures carry with them a small but important perioperative risk, but they are very successful in providing patients with immediate relief from the mortality and morbidity of atherosclerotic cardiovascular disease. Despite these very encouraging results, repeat CABG procedures are frequently necessary, as indicated by a clear increase in the number of patients who eventually undergo second and even third procedures; the perioperative mortality and morbidity seen in primary CABG procedures is increased in these re-do procedures.

There have been improvements in minimally invasive surgical techniques for uncomplicated CAD. However, nearly all CABG procedures performed for valvular and/or congenital heart disease, heart transplantation, and major aortic procedures, are still carried out on patients supported by CPB. In CPB, large cannulae are inserted into the great vessels of a patient to permit mechanical pumping and oxygenation of the blood using a membrane oxygenator. The blood is returned to the patient without flowing through the lungs, which are hypoperfused during this procedure. The heart is stopped using a cardioplegic solution, the patient cooled to help prevent brain damage, and the peripheral circulating volume increased by an extracorporeal circuit, i.e., the CPB circuit, which requires "priming" with donor blood and saline mixtures are used to fill the extracorporeal circuit. CPB has been extensively used in a variety of procedures performed for nearly half a century with successful outcomes. The interaction between artificial surfaces, blood cells, blood proteins, damaged vascular endothelium, and extravascular tissues, such as bone, disturbs hemostasis and frequently activates the CAS, which, as noted above, can result in a variety of disruptions in the blood and vasculature. Such disruption leads to excess perioperative bleeding, which then requires immediate blood transfusion. A consequence of circulating whole blood through an extracorporeal circuit in CPB can also include the systemic inflammatory response (SIR), which is initiated by contact activation of the coagulation and complement systems. Indeed, much of the morbidity and mortality associated with seemingly mechanically successful CPB surgical procedures is the result of the effects of activating coagulation, fibrinolysis, or complement systems. Such activation can damage the pulmonary system, leading to adult respiratory distress syndrome (ARDS), impairment of kidney and splanchnic circulation, and induction of a general coagulopathy leading to blood loss and the need for transfusions. In addition to the dangers of perioperative blood loss, additional pathologies associated with SIR include neurocognitive deficits, stroke, renal failure, acute myocardial infarct, and cardiac tissue damage.

Blood transfusions also present a significant risk of infection and elevate the cost of CABG or other similar procedures that require CPB. In the absence of any pharmacological intervention, three to seven units of blood must typically be expended on a patient, even with excellent surgical techniques. Accordingly, there is considerable incentive for the development of new and improved pharmacologically effective compounds to reduce or prevent perioperative bleeding and SIR in patients subjected to CPB and CABG procedures.

Administration and Dosing Considerations for KI Polypeptides

KI polypeptides described herein can be administered to a patient before, during, and/or after a surgical procedure in a pharmaceutically acceptable composition. The term "pharmaceutically acceptable" composition refers to a non-toxic carrier or excipient that may be administered to a patient, together with a compound of this invention, and wherein the carrier or excipient not destroy the biological or pharmacological activity of the composition. KI polypeptides described herein can be administered locally or systemically by any suitable means for delivery of a kallikrein inhibitory amount of the KI polypeptides to a patient including but not limited to systemic administrations such as, for example, intravenous and inhalation. Parenteral administration is particularly preferred.

For parenteral administration, the polypeptides can be injected intravenously, intramuscularly, intraperitoneally, or subcutaneously. Intravenous administration is preferred. Typically, compositions for intravenous administration are solutions in sterile isotonic aqueous buffer. Other pharmaceutically acceptable carriers include, but are not limited to, sterile water, saline solution, and buffered saline (including buffers like phosphate or acetate), alcohol, vegetable oils, polyethylene glycols, gelatin, lactose, amylose, magnesium stearate, talc, silicic acid, paraffin, etc. Where necessary, the composition can also include a solubilizing agent and a local anaesthetic such as lidocaine to ease pain at the site of the injection, preservatives, stabilizers, wetting agents, emulsifiers, salts, lubricants, etc. as long as they do not react deleteriously with the active compounds. Similarly, tie composition can comprise conventional excipients, e.g., pharmaceutically acceptable organic or inorganic carrier substances suitable for parenteral, enteral or intranasal application which do not deleteriously react with the active compounds. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline can be provided so that the ingredients can be mixed prior to administration.

Preferably, the methods of the invention comprise administering a KI polypeptide to a patient as an intravenous infusion according to any approved procedure. Thus, a KI polypeptide described herein can be administered to a patient subjected to a CABG procedure at the times similar to those currently used in approved protocols for administering aprotinin and in an amount necessary to provide a patient with a required number or concentration of kallikrein inhibitory units (KIU). According to the invention, a KI polypeptide described herein can also be administered to a patient in the immediate postoperative period, when bleeding abnormalities can occur as a consequence of downstream effects of SIR. For example, in a procedure involving CPB, a KI polypeptide described herein can be administered to a patient as an initial loading dose, e.g., an effective amount over the course of a convenient time, such as 10 minutes, prior to induction of anesthesia. Then, at induction of anesthesia, a second dose of KI polypeptide can be injected into the CPB priming fluid ("pump prime volume"). The patient can then be placed on a continuous and controlled intravenous infusion dose for the duration of the surgical procedure, and after the procedure if indicated.

Currently there are two regimens approved in the United States for administering aprotinin to a patient undergoing a CABG procedure (see, product label and insert for TRASYLOL®, Bayer Corporation Pharmaceutical Division, West Haven, Conn.). One such approved regimen uses a 2 million KIU intravenous loading dose, 2 million KIU into the pump prime volume, and 500,000 KIU per hour of surgery. Another approved regimen uses 1 million KIU intravenous loading dose, 1 million KIU into the pump prime volume, and 250,000 KIU per hour of surgery. As these regimens are based on KIU, the regimens are readily adapted to any KI polypeptide described herein once the specific activity and KIU of a particular KI polypeptide has been determined by standard assays. Owing to the enhanced binding affinity and inhibitory activity in representative KI polypeptides described herein relative to aprotinin, it is expected that such compositions and methods of the invention are likely to require fewer milligrams (mg) per patient to provide a patient with the required number or concentration of KIU.

Several considerations regarding dosing with a KI polypeptide in methods of the invention can be illustrated by way of example with the representative PEP-1 KI polypeptide of the invention having the amino sequence of SEQ ID NO:2 (molecular weight of 7,054 Daltons).

Table 1, below, provides a comparison of the affinity ($K_{i,app}$) of the PEP-1 KI polypeptide for kallikrein and eleven other known plasma proteases.

TABLE 1

| Protease Substrate | PEP-1 $K_{i,app}$ (pM) | Aprotinin $K_{i,app}$ (pM) |
|---|---|---|
| human plasma kallikrein | 44 | $3.0 \times 10^4$ |
| human urine kallikrein | $>1 \times 10^8$ | $4.0 \times 10^3$ |
| porcine pancreatic kallikrein | $2.7 \times 10^7$ | 550 |
| human C1r, activated | $>2.0 \times 10^8$ | $>1.0 \times 10^7$ |
| human C1s, activated | $>2.0 \times 10^7$ | $>1.0 \times 10^8$ |
| human plasma factor XIa | $1.0 \times 10^4$ | ND |
| human plasma factor XIIa | $>2.0 \times 10^7$ | $>1.0 \times 10^8$ |
| human plasmin | $1.4 \times 10^5$ | 894 |
| human pancreatic trypsin | $>2 \times 10^7$ | ND |
| human pancreatic chymotrypsin | $>2.0 \times 10^7$ | $7.3 \times 10^5$ |
| human neutrophil elastase | $>2.0 \times 10^7$ | $1.7 \times 10^6$ |
| human plasma thrombin | $>2.0 \times 10^7$ | $>1.0 \times 10^8$ |

ND = not determined

Clearly, the PEP-1 KI polypeptide is highly specific for human plasma kallikrein. Furthermore, the affinity ($K_{i,app}$) of PEP-1 for kallikrein is 1000 times higher than the affinity of aprotinin for kallikrein: the $K_{i,app}$ of PEP-1 for kallikrein is about 44 pM (Table 1), whereas the $K_{i,app}$ of aprotinin for kallikrein is 30,000 pM. Thus, a dose of PEP-1 could be approximately 1000 times lower than that used for aprotinin on a per mole basis. However, consideration of several other factors may provide a more accurate estimation of the dose of PEP-1 required in practice. Such factors include the amount of kallikrein activated during CPB in a particular patient, the concentration of kallikrein required to elicit an SIR, and the bioavailability and pharmacological distribution of PEP-1 in a patient. Nevertheless, use of a KI polypeptide in methods according to the invention and provided in doses currently approved for the use of aprotinin is still expected to provide significant improvements over the current use of the less specific, lower affinity, bovine aprotinin.

For example, the total amount of circulating prekallikrein in plasma is estimated at approximately 500 nM (Silverberg, M. et al., "The Contact System and Its Disorders," in Blood: Principles and Practice of Hematology, Handin, R. et al., eds., J B Lippincott Co., Philadelphia, 1995). If all of the prekallikrein were activated, then at least 500 nM of PEP-1 would be required for a stoichiometric inhibition of kallikrein. An individual having 5 liters of plasma would therefore require about 18 mg of PEP-1 to achieve a plasma concentration of 500 nM.

Another factor to consider is the threshold concentration of kallikrein required to induce a SIR in a patient. If the concentration of active kallikrein must be maintained below, e.g., 1 nM, then owing to its high affinity for kallikrein, PEP-1 offers a significant advantage over aprotinin in the amount of protein that would be required to inhibit SIR. In particular, a concentration of PEP-1 of 1 nM would inhibit 99.6% of kallikrein present at 1 nM (i.e., only 0.4 pM free kallikrein remaining in the blood), whereas, an aprotinin concentration of 1 nM would only inhibit 24.5% of the kallikrein present at 1 nM. For aprotinin to inhibit 99% of the kallikrein at 1 nM, an aprotinin concentration in the plasma of at least 3.mu.M is required (i.e., 3000 times higher concentration than for PEP-1).

For a patient undergoing CPB, an initial clinical dose of PEP-1 can be estimated from a recommended dose regimen of aprotinin (1.times.10.sup.6 KIU) mentioned above. Aprotinin is reported in a package insert to have as specific inhibitory activity of 7143 KIU/mg determined using a dog blood pressure assay. Therefore, 1.times.10.sup.6 KIU is equivalent to 140 mg of aprotinin (i.e., 1.times.10.sup.6 KIU/7143 KIU/mg=140 mg of aprotinin). In a patient having a blood plasma volume of 5 liters, 140 mg corresponds to approximately 4.3.mu.M aprotinin (molecular weight of aprotinin is 6512 Daltons). The specific activity of aprotinin in the standard inhibitory assay used for PEP-1 is 0.4 KIU/mg of polypeptide. A dose of 140 mg would correspond to a loading dose for aprotinin of 56 KIU (140 mg.times.0.4 KIU/mg=56 KIU). In contrast, since the specific activity of the PEP-1 KI polypeptide is 10 KIU/mg in the standard inhibition assay, a dose of only 5.6 mg of PEP-1 would be required to provide the number of KIUs equivalent to 140 mg of aprotinin. In a patient with a plasma volume of 5 liters, this corresponds to about 160 nM PEP-1 (molecular weight of PEP-1 is 7054 Daltons), although a higher dose of the PEP-1 KI polypeptide can be required if all of the plasma kallikrein (500 nM) is activated and/or if this KI polypeptide is poorly distributed in a patient.

Furthermore, the KI polypeptides can be non-naturally occurring, and they can be produced synthetically or recombinantly, as noted above, thereby avoiding potential contamination of transmissible diseases that can arise during isolation of a protein from a natural animal source, such as in the case of aprotinin, which is isolated from bovine lung. Increasingly important to administrative and public acceptance of a treatment or pharmaceutical composition comprising a polypeptide is the avoidance of possible contamination with and transmission to human patients of various pathological agents. Of particular interest for the safety of proteins isolated from a bovine tissue is the elimination of the possible risk of exposure to viral mediated diseases, bacterial mediated diseases, and, especially, transmissible bovine spongiform encephalopathies.

As variants of the Kunitz domain 1 of the human LACI protein, fewer side effects are expected from administering the KI polypeptides to patients than for aprotinin, which is a bovine protein that is documented to cause anaphylactic and anaphylactoid responses in patients, especially in repeat administrations, such as second time CABG procedures. Additionally, the highly specific binding of the KI polypeptides described herein to kallikrein will effectively limit or eliminate the thrombotic tendencies observed with aprotinin, and reduce the problems observed with graft patency following CABG procedures.

The invention will be further described with reference to the following non-limiting examples. The teachings of all the patents, patent applications and all other publications and websites cited herein are incorporated by reference in their entirety.

EXEMPLIFICATION

Example 1

A Representative KI Polypeptide

A non-naturally occurring, KI polypeptide useful in the compositions and methods of the invention was identified as a kallikrein binding polypeptide displayed on a recombinant phage from a phage display library. PEP-1 has the following amino acid sequence: Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gin Asn Arg Phe Glu Ser Leu Glu Glu Cys Lys Lys Met Cys Thr Arg Asp (SEQ ID NO:2). The molecular weight of PEP-1 is 7,054 Daltons.

The nucleotide sequence (SEQ ID NO:3) encoding the PEP-1 amino acid sequence (SEQ ID NO:2), was derived from a peptide that was isolated and sequenced by standard methods determined from the recombinant phage DNA. PEP-1 was produced in amounts useful for further characterization as a recombinant protein in His4.sup.-phenotype host cells of yeast strain *Pichia pastoris*.

Example 2

Construction of a Recombinant Plasmid to Express KI Polypeptides

The initial plasmid, pHIL-D2, is ampicillin resistant and contains a wild-type allele of His4 from *P. pastoris*. The final DNA sequence comprising the coding sequence for the mat.alpha. Prepro-PEP-1 fusion protein in the recombinant expression plasmid pPIC-K503 is shown in FIG. 2. The DNA sequence of pHIL-D2 was modified to produce pPIC-K503, as follows:

1. The BstBI site in the 3' AOX1 region of pHIL-D2, located downstream of the His 4 gene, was removed by partial restriction digestion, fill-in, and ligation, altering the sequence from TTCGAA (SEQ ID NO:23) to TTCGCGAA (SEQ ID NO:24). This modification was made to facilitate and direct the cloning of the expression cassette into the plasmid.

2. The AatII site bearing the bla gene located downstream of His4 was removed by restriction digestion, fill-in, and ligation modifying the sequence from GACGTC (SEQ ID NO:25) to GACGTACGTC (SEQ ID NO:26). This modification was made to facilitate the cloning of expression cassettes having AatII sites into the plasmid. The DNA encoding PEP-1 was synthesized based on the nucleotide sequence from the original kallikrein-binding display phage and consisted of 450 base pairs (bp). The final DNA sequence of the insert in the pHIL-D2 plasmid is flanked by a 5' AOX1 sequence and a 3' AOX1 sequence (portions of which are shown in FIG. 2) and encode a fusion protein comprising the mat.alpha. prepro signal peptide of *S. cerevisiae* fused to the structural coding sequence for the PEP-1 KI polypeptide. The signal peptide was added to facilitate the secretion of PEP-1 from the yeast host cells. The oligonucleotides to form the insert were synthesized and obtained commercially (Genesis Labs, The Woodlands, Tex.), and the insert was generated by polymerase chain reaction (PCR). The linked synthetic DNA encoding the mat.alpha. prepro/PEP-1 fusion protein was then incorporated by ligation into the modified pHIL-D2 plasmid between the BstBI and EcoRI sites.

The ligation products were used to transform *Escherichia coli* strain XLI Blue. A PCR assay was used to screen *E. coli* transformants for the desired plasmid construct. DNA from cell extracts was amplified by PCR using primers containing the 5' AOX1 and 3' AOX1 sequences (see above and FIG. 2). PCR products of the correct number of base pairs were sequenced. In addition, approximately 20-50 bp on either side of the cloning sites were sequenced, and the predicted sequence was obtained. The final DNA sequence of the insert in the pHIL-D2 plasmid (to yield plasmid pPIC-K503) is shown in FIG. 2 along with portions of flanking 5' and 3' AOX1 sequences and corresponding amino acid sequence of the fusion protein comprising the mat.alpha. prepro signal peptide of *S. cerevisiae* fused to the structural coding sequence for the PEP-1 KI polypeptide. A transformant with the desired expression plasmid construct, plasmid pPIC-K503, was selected for preparing yeast cell lines for routine production of PEP-1.

Example 3

Manufacture of PEP-1 from Recombinant Yeast Cell Line

Spheroplasts of *P. pastoris* GS115 having the His4.sup.-phenotype were transformed with the expression plasmid pPIC-K503 (above) following linearization of the plasmid at the SacI site and homologous recombination of the plasmid DNA into the host 5' AOX1 locus. The phenotype of the production strain is His4.sup.+. The entire plasmid was inserted into the 5' AOX1 genomic sequence of the yeast.

Isolates from the transformation were screened for growth in the absence of exogenous histidine with methanol as the sole carbon source. Greater than 95% of the transformants retained the wild-type ability to grow with methanol as the sole carbon source, thereby demonstrating that the plasmid had been inserted into the host genome by homologous recombination rather than transplacement. These transformants did not require exogenous histidine for growth, thereby demonstrating that the plasmid had integrated into the host genome. Selected colonies were cloned. Small culture expression studies were performed to identify clones secreting the highest levels of active PEP-1 into the culture medium. PEP-1 secretion levels in clarified culture supernatant solutions were quantified for PEP-1 levels by sodium dodecyl sulfate polyacrylamide gel electrophoresis (SDS-PAGE) and evaluated for kallikrein inhibition. A yeast clone was selected for PEP-1 production based on its high level of PEP-1 expression among cultures sampled.

Master and working cell banks of *P. pastoris* producing PEP-1 were prepared commercially (MDS Pharma Services, Bothell, Wash.). A standard production of PEP-1 in yeast comprised three steps as follows: (1) preparation of the seed culture, (2) fermentation, and (3) recovery of the culture.

The seed culture step consisted of the inoculation of six flasks (300 mL each) containing sterile inoculum broth (yeast nitrogen base, potassium phosphate, and glycerol, pH=5) with the contents of a single vial of a working cell bank of *P. pastoris* producing PEP-1. Flasks were inoculated in an orbital shaker (300 rpm) for approximately 13 hours at 30.degree. C.+-2.degree. C.

Fermentations were performed in a closed 100 liter Braun fermenter filled with sterile broth. Each fermentation was initiated with the transfer of the contents of the six seed culture flasks to the fermenter. After approximately 24 hours, the glycerol in the fermenter became exhausted and additional glycerol was added for approximately 8 additional hours.

A mixed feed phase, which lasted approximately 83 hours, was then initiated by the addition of a glycerol and methanol feed. At the end of this time, the fermentation was terminated, and the fermenter contents were diluted with purified water. The purification and processing of PEP-1 consisted of five steps as follows: (1) expanded bed chromatography, (2) cation exchange chromatography, (3) hydrophobic interaction chromatography (HIC), (4) ultrafiltration and diafiltration, and (5) final filtration and packaging.

The initial purification step consisted of expanded bed chromatography. The diluted fermenter culture was applied to the equilibrated column packed with Streamline SP resin (Amersham Pharmacia Streamline 200 chromatography column, Amersham Pharmacia, Piscataway, N.J.). The column was then washed (50 mM acetic acid, pH=3.0-3.5) in an up-flow mode to flush the yeast cells from the expanded bed. The top adaptor was raised above the expanded bed enhance washing. The flow was stopped and the bed was allowed to settle. The adaptor was moved down so that it was slightly above the settled bed. The direction of the flow was reversed. The effluent was collected. Washing was continued in a downward mode using 50 mM sodium acetate, pH 4.0. The effluent was collected. PEP-1 was eluted from the column using 50 mM sodium acetate, pH 6.0. The eluate was collected in a 50 liter container. The eluate was then filtered through a 0.22.mu. filter into a clean container located in the purification site. Additional samples were collected for the determination of PEP-1 concentration. A cation exchange chromatography step was then performed using the filtered eluate from the expanded bed column. PEP-1 was eluted from the column using 15 mM trisodium citrate, pH 6.2.

Additional proteins were removed from the PEP-1 preparation by hydrophobic interaction chromatography (HIC). Prior to HIC, the eluate from the cation exchange column was diluted with ammonium sulfate. The eluate was applied to the column, and the PEP-1 was eluted using ammonium sulfate (0.572 M) in potassium phosphate (100 mM), pH 7.0. The eluate was collected in fractions based on A280 values. All fractions were collected into sterile, pre-weighed PETG bottles.

Selected fractions were pooled into a clean container. The pool was concentrated by ultrafiltration. The concentrated PEP-1 preparation was immediately diafiltered against ten volumes of PBS, pH 7.0.

A final filtration step was performed prior to packaging in order to minimize the bioburden in the bulk PEP-1. The bulk solution was filtered through a 0.22.mu. filter and collected into a sterile, pre-weighed PETG bottle. A sample was removed for lot release testing. The remainder of the bulk was dispensed aseptically into sterile PETG bottles and stored at −20.degree. C.

Example 4

Kallikrein Inhibition Assay

A kinetic test was used to measure inhibitory activity of KI polypeptides, such as PEP-1. The kinetic assay measures fluorescence following kallikrein-mediated cleavage of a substrate, prolylphenylalanylarginyl amino methyl coumarin. A known amount of kallikrein was incubated with a serially diluted KI polypeptide reference standard or serially diluted KI polypeptide test samples, in a suitable reaction buffer on a microtiter plate. Each sample was run in triplicate. The substrate solution was added, and the plate read immediately using an excitation wavelength of 360 nm and an emission wavelength of 460 nm. At least two each of the reference standard and sample curves were required to have an R-squared value of 0.95 to be considered valid.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for preventing or reducing the onset of systemic inflammatory response associated with a surgical procedure in a patient comprising: administering to the patient a kallikrein inhibitory amount of a composition comprising a polypeptide that comprises the amino acid sequence: Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (amino acids 3-60 of SEQ ID NO:2), or an amino acid sequence that is 90% identical to amino acids 3-60 of SEQ ID NO:2 wherein
   position 5 is Cys;
   position 10 is Asp;
   position 11 is Asp;
   position 12 is Gly;
   position 13 is Pro;
   position 14 is Cys;
   position 15 is Arg;
   position 16 is Ala;
   position 17 is Ala;
   position 18 is His;
   position 19 is Pro;
   position 21 is Trp;
   position 22 is Phe;
   position 23 is Phe;
   position 30 is Cys;
   position 31 is Glu;
   position 32 is Glu;
   position 33 is Phe;
   position 34 is Ile;
   position 35 is Tyr;
   position 36 is Gly;
   position 37 is Gly;
   position 38 is Cys;
   position 39 is Glu;
   position 40 is Gly;
   position 43 is Asn;
   position 45 is Phe;
   position 51 is Cys; and
   position 55 is Cys, and wherein the polypeptide inhibits kallikrein.

2. The method of claim 1, wherein the surgical procedure is a cardiothoracic surgery.

3. The method of claim 2, wherein the cardiothoracic surgery is cardiopulmonary bypass or coronary artery bypass grafting.

4. The method of claim 1, wherein the polypeptide consists of the amino acid sequence: Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:2).

5. The method of claim 4, wherein the surgical procedure is a cardiothoracic surgery.

6. The method of claim 5, wherein the cardiothoracic surgery is cardiopulmonary bypass or coronary artery bypass grafting.

7. The method of claim 4, wherein said administering is performed intravenously.

8. The method of claim 1, wherein the polypeptide consists of the amino acid sequence: Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (amino acids 3-60 of SEQ ID NO:2).

9. The method of claim 8, wherein the surgical procedure is a cardiothoracic surgery.

10. The method of claim 9, wherein the cardiothoracic surgery is cardiopulmonary bypass or coronary artery bypass grafting.

11. The method of claim 8, wherein said administering is performed intravenously.

12. The method of claim 1, wherein said administering is performed intravenously.

13. The method of claim 1, wherein the polypeptide comprises the amino acid sequence: Glu Ala Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (SEQ ID NO:2).

14. The method of claim 1, wherein the polypeptide comprises the amino acid sequence: Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (amino acids 3-60 of SEQ ID NO:2).

15. The method of claim 1, wherein the composition comprises a pharmaceutically acceptable carrier.

16. The method of claim 15, wherein the pharmaceutically acceptable carrier is a sterile isotonic aqueous buffer.

17. The method of claim 15, wherein the pharmaceutically acceptable carrier is sterile water.

* * * * *

SEQUENCE LISTING

```
<160> NUMBER OF SEQ ID NOS: 54

<210> SEQ ID NO 1
<211> LENGTH: 58
<212> TYPE: PRT
<213> ORGANISM: Artificial Sequence
<220> FEATURE:
<223> OTHER INFORMATION: Polypeptide Inhibiting Kallikrein
<220> FEATURE:
<221> NAME/KEY: VARIANT
<222> LOCATION: 1, 2, 3, 4, 6, 7, 8, 9, 20, 24, 25, 26, 27, 28, 29, 41,
      42, 44, 46, 47, 48, 49, 50, 52, 53, 54, 56, 57, 58
<223> OTHER INFORMATION: Xaa = any amino acid
<220> FEATURE:
<221> NAME/KEY: VARIANT
<222> LOCATION: 10
<223> OTHER INFORMATION: Xaa = Asp or Glu
<220> FEATURE:
<221> NAME/KEY: VARIANT
<222> LOCATION: 11
<223> OTHER INFORMATION: Xaa = Asp, Gly, Ser, Val, Asn, Ile, Ala or Thr
<220> FEATURE:
<221> NAME/KEY: VARIANT
<222> LOCATION: 13
<223> OTHER INFORMATION: Xaa = Arg, His, Pro, Asn, Ser, Thr, Ala, Gly,
      Lys or Gln
<220> FEATURE:
<221> NAME/KEY: VARIANT
<222> LOCATION: 15
<223> OTHER INFORMATION: Xaa = Arg, Lys, Ala, Ser, Gly, Met, Asn or Gln
<220> FEATURE:
<221> NAME/KEY: VARIANT
<222> LOCATION: 16
<223> OTHER INFORMATION: Xaa = Ala, Gly, Ser, Asp or Asn
```

```
<220> FEATURE:
<221> NAME/KEY: VARIANT
<222> LOCATION: 17
<223> OTHER INFORMATION: Xaa = Ala, Asn, Ser, Ile, Gly, Val, Gln or Thr
<220> FEATURE:
<221> NAME/KEY: VARIANT
<222> LOCATION: 18
<223> OTHER INFORMATION: Xaa = His, Leu, Gln or Ala
<220> FEATURE:
<221> NAME/KEY: VARIANT
<222> LOCATION: 19
<223> OTHER INFORMATION: Xaa = Pro, Gln, Leu, Asn or Ile
<220> FEATURE:
<221> NAME/KEY: VARIANT
<222> LOCATION: 21
<223> OTHER INFORMATION: Xaa = Trp, Phe, Tyr, His or Ile
<220> FEATURE:
<221> NAME/KEY: VARIANT
<222> LOCATION: 22
<223> OTHER INFORMATION: Xaa = Tyr or Phe
<220> FEATURE:
<221> NAME/KEY: VARIANT
<222> LOCATION: 23
<223> OTHER INFORMATION: Xaa = Tyr or Phe
<220> FEATURE:
<221> NAME/KEY: VARIANT
<222> LOCATION: 31
<223> OTHER INFORMATION: Xaa = Glu, Asp, Gln, Asn, Ser, Ala, Val, Leu,
    Ile or Thr
<220> FEATURE:
<221> NAME/KEY: VARIANT
<222> LOCATION: 32
<223> OTHER INFORMATION: Xaa = Glu, Gln, Asp, Asn, Pro, Thr, Leu, Ser,
    Ala, Gly or Val
<220> FEATURE:
<221> NAME/KEY: VARIANT
<222> LOCATION: 34
<223> OTHER INFORMATION: Xaa = Thr, Ile, Ser, Val, Ala, Asn, Gly or Leu
<220> FEATURE:
<221> NAME/KEY: VARIANT
<222> LOCATION: 35
<223> OTHER INFORMATION: Xaa = Tyr, Trp or Phe
<220> FEATURE:
<221> NAME/KEY: VARIANT
<222> LOCATION: 39
<223> OTHER INFORMATION: Xaa = Glu, Gly, Ala, Ser or Asp
<220> FEATURE:
<221> NAME/KEY: VARIANT
<222> LOCATION: 40
<223> OTHER INFORMATION: Xaa = Gly or Ala
<220> FEATURE:
<221> NAME/KEY: VARIANT
<222> LOCATION: 43
<223> OTHER INFORMATION: Xaa = Asn or Gly
<220> FEATURE:
<221> NAME/KEY: VARIANT
<222> LOCATION: 45
<223> OTHER INFORMATION: Xaa = Phe or Tyr

<400> SEQUENCE: 1

Xaa Xaa Xaa Xaa Cys Xaa Xaa Xaa Xaa Xaa Xaa Gly Xaa Cys Xaa Xaa
 1               5                  10                  15

Xaa Xaa Xaa Xaa Xaa Xaa Xaa Xaa Xaa Xaa Xaa Xaa Xaa Cys Xaa Xaa
            20                  25                  30

Phe Xaa Xaa Gly Gly Cys Xaa Xaa Xaa Xaa Xaa Xaa Xaa Xaa Xaa Xaa
        35                  40                  45

Xaa Xaa Cys Xaa Xaa Xaa Cys Xaa Xaa Xaa
    50                  55

<210> SEQ ID NO 2
<211> LENGTH: 60
<212> TYPE: PRT
<213> ORGANISM: Artificial Sequence
<220> FEATURE:
<223> OTHER INFORMATION: Isolated Binding Peptide
```

<400> SEQUENCE: 2

Glu Ala Met His Ser Phe Cys Ala Phe Lys Ala Asp Asp Gly Pro Cys
1               5                   10                  15

Arg Ala His Pro Arg Trp Phe Phe Asn Ile Phe Thr Arg Gln Cys
            20                  25                  30

Glu Glu Phe Ile Tyr Gly Gly Cys Glu Gly Asn Gln Asn Arg Phe Glu
            35                  40                  45

Ser Leu Glu Glu Cys Lys Lys Met Cys Thr Arg Asp
    50                  55                  60

<210> SEQ ID NO 3
<211> LENGTH: 179
<212> TYPE: DNA
<213> ORGANISM: Artificial Sequence
<220> FEATURE:
<223> OTHER INFORMATION: Coding Sequence of Pep-1

<400> SEQUENCE: 3
gaggctatgc actctttctg tgctttcaag gctgacgacg gtcgtgcaga gctgctcacc        60
caagatggtt cttcaacatc ttcacgcgtc aatgcgagga gttcatctac ggtggttgtg       120
agggtaacca aaacagattc gagtctctag aggagtgtaa gaagatgtgt actagagac        179

<210> SEQ ID NO 4
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 4

Met His Ser Phe Cys Ala Phe Lys Ala Asp Asp Gly Pro Cys Lys Ala
1               5                   10                  15

Asn His Leu Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 5
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 5

Met His Ser Phe Cys Ala Phe Lys Ala Asp Asp Gly His Cys Lys Ala
1               5                   10                  15

Asn Gln Arg Phe Phe Asn Ile Phe Thr Arg Gln Cys Glu Glu
            20                  25                  30

Phe Thr Tyr Gly Gly Cys Gly Gly Asn Gln Asn Arg Phe Glu Ser Leu
            35                  40                  45

Glu Glu Cys Lys Lys Met Cys Thr Arg Asp
    50                  55

<210> SEQ ID NO 6
<211> LENGTH: 58
<212> TYPE: PRT
<213> ORGANISM: Artificial Sequence

```
<220> FEATURE:
<223> OTHER INFORMATION: Isolated Binding Peptide

<400> SEQUENCE: 6

Met His Ser Phe Cys Ala Phe Lys Ala Asp Asp Gly His Cys Lys Ala
1               5                   10                  15

Asn His Gln Arg Phe Phe Asn Ile Phe Thr Arg Gln Cys Glu Gln
            20                  25                  30

Phe Thr Tyr Gly Gly Cys Ala Gly Asn Gln Asn Arg Phe Glu Ser Leu
        35                  40                  45

Glu Glu Cys Lys Lys Met Cys Thr Arg Asp
    50                  55

<210> SEQ ID NO 7
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 7

Met His Ser Phe Cys Ala Phe Lys Ala Asp Asp Gly His Cys Lys Ala
1               5                   10                  15

Ser Leu Pro Arg Phe Phe Asn Ile Phe Thr Arg Gln Cys Glu Glu
            20                  25                  30

Phe Ile Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 8
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 8

Met His Ser Phe Cys Ala Phe Lys Ala Asp Asp Gly His Cys Lys Ala
1               5                   10                  15

Asn His Gln Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 9
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 9

Met His Ser Phe Cys Ala Phe Lys Ala Asp Asp Gly His Cys Lys Gly
1               5                   10                  15

Ala His Leu Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45
```

Glu Glu Cys Lys Lys Met Cys Thr Arg Asp
        50                  55

<210> SEQ ID NO 10
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 10

Met His Ser Phe Cys Ala Phe Lys Ala Asp Asp Gly Arg Cys Lys Gly
  1               5                  10                  15

Ala His Leu Arg Phe Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
        50                  55

<210> SEQ ID NO 11
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 11

Met His Ser Phe Cys Ala Phe Lys Ala Asp Gly Gly Arg Cys Arg Gly
  1               5                  10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
        50                  55

<210> SEQ ID NO 12
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 12

Met His Ser Phe Cys Ala Phe Lys Ala Asp Asp Gly Pro Cys Arg Ala
  1               5                  10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
        50                  55

<210> SEQ ID NO 13
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 13

Met His Ser Phe Cys Ala Phe Lys Ala Asp Val Gly Arg Cys Arg Gly

```
                1               5                  10                 15
Ala His Pro Arg Trp Phe Phe Asn Ile Phe Thr Arg Gln Cys Glu Glu
                20                 25                 30

Phe Ser Tyr Gly Gly Cys Gly Gly Asn Gln Asn Arg Phe Glu Ser Leu
            35                 40                 45

Glu Glu Cys Lys Lys Met Cys Thr Arg Asp
        50                 55

<210> SEQ ID NO 14
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 14

Met His Ser Phe Cys Ala Phe Lys Ala Asp Val Gly Arg Cys Arg Gly
  1               5                 10                 15

Ala Gln Pro Arg Phe Phe Phe Asn Ile Phe Thr Arg Gln Cys Glu Glu
                20                 25                 30

Phe Ser Tyr Gly Gly Cys Gly Gly Asn Gln Asn Arg Phe Glu Ser Leu
            35                 40                 45

Glu Glu Cys Lys Lys Met Cys Thr Arg Asp
        50                 55

<210> SEQ ID NO 15
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 15

Met His Ser Phe Cys Ala Phe Lys Ala Asp Asp Gly Ser Cys Arg Ala
  1               5                 10                 15

Ala His Leu Arg Trp Phe Phe Asn Ile Phe Thr Arg Gln Cys Glu Glu
                20                 25                 30

Phe Ser Tyr Gly Gly Cys Gly Gly Asn Gln Asn Arg Phe Glu Ser Leu
            35                 40                 45

Glu Glu Cys Lys Lys Met Cys Thr Arg Asp
        50                 55

<210> SEQ ID NO 16
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 16

Met His Ser Phe Cys Ala Phe Lys Ala Glu Gly Gly Ser Cys Arg Ala
  1               5                 10                 15

Ala His Gln Arg Trp Phe Phe Asn Ile Phe Thr Arg Gln Cys Glu Glu
                20                 25                 30

Phe Ser Tyr Gly Gly Cys Gly Gly Asn Gln Asn Arg Phe Glu Ser Leu
            35                 40                 45

Glu Glu Cys Lys Lys Met Cys Thr Arg Asp
        50                 55

<210> SEQ ID NO 17
<211> LENGTH: 58
```

```
<212> TYPE: PRT
<213> ORGANISM: Artificial Sequence
<220> FEATURE:
<223> OTHER INFORMATION: Isolated Binding Peptide

<400> SEQUENCE: 17

Met His Ser Phe Cys Ala Phe Lys Ala Asp Asp Gly Pro Cys Arg Gly
1               5                   10                  15

Ala His Leu Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 18
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 18

Met His Ser Phe Cys Ala Phe Lys Ala Asp Asp Gly His Cys Arg Gly
1               5                   10                  15

Ala Leu Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 19
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 19

Met His Ser Phe Cys Ala Phe Lys Ala Asp Ser Gly Asn Cys Arg Gly
1               5                   10                  15

Asn Leu Pro Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 20
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 20

Met His Ser Phe Cys Ala Phe Lys Ala Asp Ser Gly Arg Cys Arg Gly
1               5                   10                  15

Asn His Gln Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
```

```
                       35              40              45

Glu Glu Cys Lys Lys Met Cys Thr Arg Asp
    50                  55

<210> SEQ ID NO 21
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 21

Met His Ser Phe Cys Ala Phe Lys Ala Asp Gly Gly Arg Cys Arg Ala
1               5                   10                  15

Ile Gln Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 22
<211> LENGTH: 58
<212> TYPE: PRT
<213> ORGANISM: Artificial Sequence
<220> FEATURE:
<223> OTHER INFORMATION: Isolated Binding Peptide

<400> SEQUENCE: 22

Met His Ser Phe Cys Ala Phe Lys Ala Asp Asp Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 23
<211> LENGTH: 6
<212> TYPE: DNA
<213> ORGANISM: Artificial Sequence
<220> FEATURE:
<223> OTHER INFORMATION: Modified Cloning Site

<400> SEQUENCE: 23 ttcgaa                                                          6

<210> SEQ ID NO 24
<211> LENGTH: 8
<212> TYPE: DNA
<213> ORGANISM: Artificial Sequence
<220> FEATURE:
<223> OTHER INFORMATION: Modified Cloning Site

<400> SEQUENCE: 24 ttcgcgaa                                                        8

<210> SEQ ID NO 25
<211> LENGTH: 6
<212> TYPE: DNA
<213> ORGANISM: Artificial Sequence
<220> FEATURE:
<223> OTHER INFORMATION: Modified Cloning Site
```

```
<400> SEQUENCE: 25 gacgtc                                                                    6

<210> SEQ ID NO 26
<211> LENGTH: 10
<212> TYPE: DNA
<213> ORGANISM: Artificial Sequence
<220> FEATURE:
<223> OTHER INFORMATION: Modified Cloning Site

<400> SEQUENCE: 26
gacgtacgtc                                                               10

<210> SEQ ID NO 27
<211> LENGTH: 548
<212> TYPE: DNA
<213> ORGANISM: Artificial Sequence
<220> FEATURE:
<223> OTHER INFORMATION: Nucleotide Sequence of Fusion Protein

<400> SEQUENCE: 27
cgacttttaa cgacaacttg agaagatcaa aaaacaacta attattcgaa acgatgagat        60
tcccatctat cttcactgct gttttgttcg ctgcttcctc tgctttggct gctccagtta       120
acaccactac tgaagacgag actgctcaaa ttcctgctga gctgtcatc ggttactctg        180 acttggaagg tgacttcgac gtcgctgttt tgccattctc taactctact aacaacggtt      240
tgttgttcat caacactacc atcgcttcta tcgctgctaa ggaggaaggt gtttccctcg      300
agaagagaga ggctatgcac tctttctgtg ctttcaaggc tgacgacggt ccgtgcagag      360
ctgctcaccc aagatggttc ttcaacatct tcacgcgtca atgcgaggag ttcatctacg      420
gtggttgtga gggtaaccaa aacagattcg agtctctaga ggagtgtaag aagatgtgta      480
ctagagacta gtaagaattc gccttagaca tgactgttcc tcagttcaag ttgggcactt      540
acgagaag                                                               548

<210> SEQ ID NO 28
<211> LENGTH: 145
<212> TYPE: PRT
<213> ORGANISM: Artificial Sequence
<220> FEATURE:
<223> OTHER INFORMATION: Fusion Protein

<400> SEQUENCE: 28

Met Arg Phe Pro Ser Ile Phe Thr Ala Val Leu Phe Ala Ala Ser Ser
  1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Met His Ser Phe Cys Ala Phe Lys Ala
                 85                  90                  95

Asp Asp Gly Pro Cys Arg Ala Ala His Pro Arg Trp Phe Phe Asn Ile
            100                 105                 110

Phe Thr Arg Gln Cys Glu Glu Phe Ile Tyr Gly Gly Cys Glu Gly Asn
        115                 120                 125
```

Gln Asn Arg Phe Glu Ser Leu Glu Glu Cys Lys Lys Met Cys Thr Arg
    130                 135                 140

Asp
145

<210> SEQ ID NO 29
<211> LENGTH: 58
<212> TYPE: PRT
<213> ORGANISM: Artificial Sequence
<220> FEATURE:
<223> OTHER INFORMATION: BPTI Sequence

<400> SEQUENCE: 29

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
                20                  25                  30

Phe Val Tyr Gly Gly Cys Arg Ala Lys Arg Asn Asn Phe Lys Ser Ala
            35                  40                  45

Glu Asp Cys Met Arg Thr Cys Gly Gly Ala
        50                  55

<210> SEQ ID NO 30
<211> LENGTH: 58
<212> TYPE: PRT
<213> ORGANISM: Artificial Sequence
<220> FEATURE:
<223> OTHER INFORMATION: ITI-D1 Sequence

<400> SEQUENCE: 30

Lys Glu Asp Ser Cys Gln Leu Gly Tyr Ser Ala Gly Pro Cys Met Gly
1               5                   10                  15

Met Thr Ser Arg Tyr Phe Tyr Asn Gly Thr Ser Met Ala Cys Glu Thr
                20                  25                  30

Phe Gln Tyr Gly Gly Cys Met Gly Asn Gly Asn Asn Phe Val Thr Glu
            35                  40                  45

Lys Glu Cys Leu Gln Thr Cys Arg Thr Val
        50                  55

<210> SEQ ID NO 31
<211> LENGTH: 58
<212> TYPE: PRT
<213> ORGANISM: Artificial Sequence
<220> FEATURE:
<223> OTHER INFORMATION: ITI-D2 Sequence

<400> SEQUENCE: 31

Thr Val Ala Ala Cys Asn Leu Pro Ile Val Arg Gly Pro Cys Arg Ala
1               5                   10                  15

Phe Ile Gln Leu Trp Ala Phe Asp Ala Val Lys Gly Lys Cys Val Leu
                20                  25                  30

Phe Pro Tyr Gly Gly Cys Gln Gly Asn Gly Asn Lys Phe Tyr Ser Glu
            35                  40                  45

Lys Glu Cys Arg Glu Tyr Cys Gly Val Pro
        50                  55

<210> SEQ ID NO 32
<211> LENGTH: 58
<212> TYPE: PRT
<213> ORGANISM: Artificial Sequence
<220> FEATURE:
<223> OTHER INFORMATION: LACI-D1 Sequence

<400> SEQUENCE: 32

Met His Ser Phe Cys Ala Phe Lys Ala Asp Asp Gly Pro Cys Lys Ala
1               5                   10                  15

Ile Met Lys Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
            35                  40                  45

Glu Glu Cys Lys Lys Met Cys Thr Arg Asp
        50                  55

<210> SEQ ID NO 33
<211> LENGTH: 58
<212> TYPE: PRT
<213> ORGANISM: Artificial Sequence
<220> FEATURE:
<223> OTHER INFORMATION: LACI-D2 Sequence

<400> SEQUENCE: 33

Lys Pro Asp Phe Cys Phe Leu Glu Glu Asp Pro Gly Ile Cys Arg Gly
1               5                   10                  15

Tyr Ile Thr Arg Tyr Phe Tyr Asn Asn Gln Thr Lys Gln Cys Glu Arg
            20                  25                  30

Phe Lys Tyr Gly Gly Cys Leu Gly Asn Met Asn Asn Phe Glu Thr Leu
            35                  40                  45

Glu Glu Cys Lys Asn Ile Cys Glu Asp Gly
        50                  55

<210> SEQ ID NO 34
<211> LENGTH: 58
<212> TYPE: PRT
<213> ORGANISM: Artificial Sequence
<220> FEATURE:
<223> OTHER INFORMATION: LACI-D3 Sequence

<400> SEQUENCE: 34

Gly Pro Ser Trp Cys Leu Thr Pro Ala Asp Arg Gly Leu Cys Arg Ala
1               5                   10                  15

Asn Glu Asn Arg Phe Tyr Tyr Asn Ser Val Ile Gly Lys Cys Arg Pro
            20                  25                  30

Phe Lys Tyr Ser Gly Cys Gly Gly Asn Glu Asn Asn Phe Thr Ser Lys
            35                  40                  45

Gln Glu Cys Leu Arg Ala Cys Lys Lys Gly
        50                  55

<210> SEQ ID NO 35
<211> LENGTH: 58
<212> TYPE: PRT
<213> ORGANISM: Artificial Sequence
<220> FEATURE:
<223> OTHER INFORMATION: HKI B9 Sequence

<400> SEQUENCE: 35

Leu Pro Asn Val Cys Ala Phe Pro Met Glu Lys Gly Pro Cys Gln Thr
1               5                   10                  15

Tyr Met Thr Arg Trp Phe Phe Asn Phe Glu Thr Gly Glu Cys Glu Leu
            20                  25                  30

Phe Ala Tyr Gly Gly Cys Gly Gly Asn Ser Asn Asn Phe Leu Arg Lys
            35                  40                  45

Glu Lys Cys Glu Lys Phe Cys Lys Phe Thr
        50                  55

```
<210> SEQ ID NO 36
<211> LENGTH: 58
<212> TYPE: PRT
<213> ORGANISM: Artificial Sequence
<220> FEATURE:
<223> OTHER INFORMATION: C alpha 3 Sequence

<400> SEQUENCE: 36

Glu Thr Asp Ile Cys Lys Leu Pro Lys Asp Glu Gly Thr Cys Arg Asp
 1               5                  10                  15

Phe Ile Leu Lys Trp Tyr Tyr Asp Pro Asn Thr Lys Ser Cys Ala Arg
            20                  25                  30

Phe Trp Tyr Gly Gly Cys Gly Gly Asn Glu Asn Lys Phe Gly Ser Gln
        35                  40                  45

Lys Glu Cys Glu Lys Val Cys Ala Pro Val
    50                  55

<210> SEQ ID NO 37
<211> LENGTH: 58
<212> TYPE: PRT
<213> ORGANISM: Artificial Sequence
<220> FEATURE:
<223> OTHER INFORMATION: TFPI-2 D1 Sequence

<400> SEQUENCE: 37

Asn Ala Glu Ile Cys Leu Leu Pro Leu Asp Tyr Gly Pro Cys Arg Ala
 1               5                  10                  15

Leu Leu Leu Arg Tyr Tyr Tyr Asp Arg Tyr Thr Gln Ser Cys Arg Gln
            20                  25                  30

Phe Leu Tyr Gly Gly Cys Glu Gly Asn Ala Asn Asn Phe Tyr Thr Trp
        35                  40                  45

Glu Ala Cys Asp Asp Ala Cys Trp Arg Ile
    50                  55

<210> SEQ ID NO 38
<211> LENGTH: 61
<212> TYPE: PRT
<213> ORGANISM: Artificial Sequence
<220> FEATURE:
<223> OTHER INFORMATION: TFPI-2 D2 Sequence

<400> SEQUENCE: 38

Val Pro Lys Val Cys Arg Leu Gln Val Ser Val Asp Asp Gln Cys Glu
 1               5                  10                  15

Gly Ser Thr Glu Lys Tyr Phe Phe Asn Leu Ser Ser Met Thr Cys Glu
            20                  25                  30

Lys Phe Phe Ser Gly Gly Cys His Arg Asn Arg Ile Glu Asn Arg Phe
        35                  40                  45

Pro Asp Glu Ala Thr Cys Met Gly Phe Cys Ala Pro Lys
    50                  55                  60

<210> SEQ ID NO 39
<211> LENGTH: 58
<212> TYPE: PRT
<213> ORGANISM: Artificial Sequence
<220> FEATURE:
<223> OTHER INFORMATION: TFPI-2 D3 Sequence

<400> SEQUENCE: 39

Ile Pro Ser Phe Cys Tyr Ser Pro Lys Asp Glu Gly Leu Cys Ser Ala
 1               5                  10                  15
```

```
Asn Val Thr Arg Tyr Tyr Phe Asn Pro Arg Tyr Arg Thr Cys Asp Ala
            20                  25                  30

Phe Thr Tyr Thr Gly Cys Gly Gly Asn Asp Asn Phe Val Ser Arg
        35                  40                  45

Glu Asp Cys Lys Arg Ala Cys Ala Lys Ala
 50                  55

<210> SEQ ID NO 40
<211> LENGTH: 59
<212> TYPE: PRT
<213> ORGANISM: Artificial Sequence
<220> FEATURE:
<223> OTHER INFORMATION: APP-I Sequence

<400> SEQUENCE: 40

Arg Asn Arg Glu Val Cys Ser Glu Gln Ala Glu Thr Gly Pro Cys Arg
 1               5                   10                  15

Ala Met Ile Ser Arg Trp Tyr Phe Asp Val Thr Glu Gly Lys Cys Ala
            20                  25                  30

Pro Phe Phe Tyr Gly Gly Cys Gly Gly Asn Arg Asn Asn Phe Asp Thr
        35                  40                  45

Glu Glu Tyr Cys Met Ala Val Cys Gly Ser Ala
 50                  55

<210> SEQ ID NO 41
<211> LENGTH: 58
<212> TYPE: PRT
<213> ORGANISM: Artificial Sequence
<220> FEATURE:
<223> OTHER INFORMATION: EpiNE7 Sequence

<400> SEQUENCE: 41

Arg Pro Asp Phe Cys Leu Glu Pro Pro Tyr Thr Gly Pro Cys Val Ala
 1               5                   10                  15

Met Phe Pro Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
        35                  40                  45

Glu Asp Cys Met Arg Thr Cys Gly Gly Ala
 50                  55

<210> SEQ ID NO 42
<211> LENGTH: 58
<212> TYPE: PRT
<213> ORGANISM: Artificial Sequence
<220> FEATURE:
<223> OTHER INFORMATION: BITI-E7-141 Sequence

<400> SEQUENCE: 42

Arg Pro Asp Phe Cys Gln Leu Gly Tyr Ser Ala Gly Pro Cys Val Ala
 1               5                   10                  15

Met Phe Pro Arg Tyr Phe Tyr Asn Gly Thr Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
 50                  55

<210> SEQ ID NO 43
<211> LENGTH: 58
<212> TYPE: PRT
<213> ORGANISM: Artificial Sequence
```

<220> FEATURE:
<223> OTHER INFORMATION: MUTT26A Sequence

<400> SEQUENCE: 43

Arg Pro Asp Phe Cys Gln Leu Gly Tyr Ser Ala Gly Pro Cys Val Ala
1               5                   10                  15

Met Phe Pro Arg Tyr Phe Tyr Asn Gly Ala Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 44
<211> LENGTH: 58
<212> TYPE: PRT
<213> ORGANISM: Artificial Sequence
<220> FEATURE:
<223> OTHER INFORMATION: MUTQE Sequence

<400> SEQUENCE: 44

Arg Pro Asp Phe Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Glu Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 45
<211> LENGTH: 58
<212> TYPE: PRT
<213> ORGANISM: Artificial Sequence
<220> FEATURE:
<223> OTHER INFORMATION: MUT1619 Sequence

<400> SEQUENCE: 45

Arg Pro Asp Phe Cys Gln Leu Gly Tyr Ser Ala Gly Pro Cys Val Gly
1               5                   10                  15

Met Phe Ser Arg Tyr Phe Tyr Asn Gly Thr Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 46
<211> LENGTH: 62
<212> TYPE: PRT
<213> ORGANISM: Artificial Sequence
<220> FEATURE:
<223> OTHER INFORMATION: EPI-HNE-1 Sequence

<400> SEQUENCE: 46

Glu Ala Glu Ala Arg Pro Asp Phe Cys Leu Glu Pro Pro Tyr Thr Gly
1               5                   10                  15

Pro Cys Ile Ala Phe Phe Pro Arg Tyr Phe Tyr Asn Ala Lys Ala Gly
            20                  25                  30

Leu Cys Gln Thr Phe Val Tyr Gly Gly Cys Met Gly Asn Gly Asn Asn
        35                  40                  45

```
Phe Lys Ser Ala Glu Asp Cys Met Arg Thr Cys Gly Gly Ala
    50                  55                  60
```

<210> SEQ ID NO 47
<211> LENGTH: 56
<212> TYPE: PRT
<213> ORGANISM: Artificial Sequence
<220> FEATURE:
<223> OTHER INFORMATION: EPI-HNE-2 Sequence

<400> SEQUENCE: 47

```
Ala Ala Cys Asn Leu Pro Ile Val Arg Gly Pro Cys Ile Ala Phe Phe
 1               5                  10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55
```

<210> SEQ ID NO 48
<211> LENGTH: 56
<212> TYPE: PRT
<213> ORGANISM: Artificial Sequence
<220> FEATURE:
<223> OTHER INFORMATION: EPI-HNE-3 Sequence

<400> SEQUENCE: 48

```
Ala Ala Cys Asn Leu Pro Ile Val Arg Gly Pro Cys Ile Ala Phe Phe
 1               5                  10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55
```

<210> SEQ ID NO 49
<211> LENGTH: 56
<212> TYPE: PRT
<213> ORGANISM: Artificial Sequence
<220> FEATURE:
<223> OTHER INFORMATION: EPI-HNE-4 Sequence

<400> SEQUENCE: 49

```
Glu Ala Cys Asn Leu Pro Ile Val Arg Gly Pro Cys Ile Ala Phe Phe
 1               5                  10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55
```

<210> SEQ ID NO 50
<211> LENGTH: 60
<212> TYPE: PRT
<213> ORGANISM: Artificial Sequence
<220> FEATURE:
<223> OTHER INFORMATION: DPI14 KR Sequence

<400> SEQUENCE: 50

```
Glu Ala Val Arg Glu Val Cys Ser Glu Gln Ala Glu Thr Gly Pro Cys
```

```
                1               5                  10                  15
Ile Ala Phe Phe Pro Arg Trp Tyr Phe Asp Val Thr Glu Gly Lys Cys
                20                  25                  30

Ala Pro Phe Phe Tyr Gly Gly Cys Gly Gly Asn Arg Asn Asn Phe Asp
                35                  40                  45

Thr Glu Glu Tyr Cys Met Ala Val Cys Gly Ser Ala
                50                  55              60

<210> SEQ ID NO 51
<211> LENGTH: 60
<212> TYPE: PRT
<213> ORGANISM: Artificial Sequence
<220> FEATURE:
<223> OTHER INFORMATION: DPI24 KR Sequence

<400> SEQUENCE: 51

Glu Ala Asn Ala Glu Ile Cys Leu Leu Pro Leu Asp Tyr Gly Pro Cys
1               5                   10                  15

Ile Ala Phe Phe Pro Arg Tyr Tyr Asp Arg Tyr Thr Gln Ser Cys
                20                  25                  30

Arg Gln Phe Leu Tyr Gly Gly Cys Glu Gly Asn Ala Asn Asn Phe Tyr
                35                  40                  45

Thr Trp Glu Ala Cys Asp Asp Ala Cys Trp Arg Ile
                50                  55              60

<210> SEQ ID NO 52
<211> LENGTH: 60
<212> TYPE: PRT
<213> ORGANISM: Artificial Sequence
<220> FEATURE:
<223> OTHER INFORMATION: DPI68 KR Sequence

<400> SEQUENCE: 52

Glu Ala Lys Pro Asp Phe Cys Phe Leu Glu Glu Asp Pro Gly Ile Cys
1               5                   10                  15

Ile Gly Phe Phe Pro Arg Tyr Phe Tyr Asn Asn Gln Ala Lys Gln Cys
                20                  25                  30

Glu Arg Phe Val Tyr Gly Gly Cys Leu Gly Asn Met Asn Asn Phe Glu
                35                  40                  45

Thr Leu Glu Glu Cys Lys Asn Ile Cys Glu Asp Gly
                50                  55              60

<210> SEQ ID NO 53
<211> LENGTH: 60
<212> TYPE: PRT
<213> ORGANISM: Artificial Sequence
<220> FEATURE:
<223> OTHER INFORMATION: DPI84 KR Sequence

<400> SEQUENCE: 53

Glu Ala Glu Thr Asp Ile Cys Lys Leu Pro Lys Asp Glu Gly Thr Cys
1               5                   10                  15

Ile Ala Phe Phe Pro Arg Trp Tyr Tyr Asp Pro Asn Thr Lys Ser Cys
                20                  25                  30

Ala Arg Phe Val Tyr Gly Gly Cys Gly Gly Asn Glu Asn Lys Phe Gly
                35                  40                  45

Ser Gln Lys Glu Cys Glu Lys Val Cys Ala Pro Val
                50                  55              60

<210> SEQ ID NO 54
<211> LENGTH: 58
```

```
<212> TYPE: PRT
<213> ORGANISM: Artificial Sequence
<220> FEATURE:
<223> OTHER INFORMATION: VARIANT
<220> FEATURE:
<221> NAME/KEY: VARIANT
<222> LOCATION: 10
<223> OTHER INFORMATION: Xaa = Asp or Glu
<220> FEATURE:
<221> NAME/KEY: VARIANT
<222> LOCATION: 11
<223> OTHER INFORMATION: Xaa = Asp, Gly, Ser, Val, Asn, Ile, Ala or Thr
<220> FEATURE:
<221> NAME/KEY: VARIANT
<222> LOCATION: 13
<223> OTHER INFORMATION: Xaa = Arg, His, Pro, Asn, Ser, Thr, Ala, Gly,
      Lys or Gln
<220> FEATURE:
<221> NAME/KEY: VARIANT
<222> LOCATION: 15
<223> OTHER INFORMATION: Xaa = Arg, Ala, Ser, Gly, Met, Asn or Gln
<220> FEATURE:
<221> NAME/KEY: VARIANT
<222> LOCATION: 16
<223> OTHER INFORMATION: Xaa = Ala, Gly, Ser, Asp or Asn
<220> FEATURE:
<221> NAME/KEY: VARIANT
<222> LOCATION: 17
<223> OTHER INFORMATION: Xaa = Ala, Asn, Ser, Ile, Gly, Val, Gln or Thr
<220> FEATURE:
<221> NAME/KEY: VARIANT
<222> LOCATION: 18
<223> OTHER INFORMATION: Xaa = His, Leu, Gln or Ala
<220> FEATURE:
<221> NAME/KEY: VARIANT
<222> LOCATION: 19
<223> OTHER INFORMATION: Xaa = Pro, Gln, Leu, Asn or Ile
<220> FEATURE:
<221> NAME/KEY: VARIANT
<222> LOCATION: 21
<223> OTHER INFORMATION: Xaa = Trp, Phe, Tyr, His or Ile
<220> FEATURE:
<221> NAME/KEY: VARIANT
<222> LOCATION: 31
<223> OTHER INFORMATION: Xaa = Glu, Asp, Gln, Asn, Ser, Ala, Val, Leu,
      Ile or Thr
<220> FEATURE:
<221> NAME/KEY: VARIANT
<222> LOCATION: 32
<223> OTHER INFORMATION: Xaa = Glu, Gln, Asp, Asn, Pro, Thr, Leu, Ser,
      Ala, Gly or Val
<220> FEATURE:
<221> NAME/KEY: VARIANT
<222> LOCATION: 34
<223> OTHER INFORMATION: Xaa = Thr, Ile, Ser, Val, Ala, Asn, Gly or Leu
<220> FEATURE:
<221> NAME/KEY: VARIANT
<222> LOCATION: 35
<223> OTHER INFORMATION: Xaa = Tyr, Trp or Phe
<220> FEATURE:
<221> NAME/KEY: VARIANT
<222> LOCATION: 39
<223> OTHER INFORMATION: Xaa = Glu, Gly, Ala, Ser or Asp

<400> SEQUENCE: 54

Met His Ser Phe Cys Ala Phe Lys Ala Xaa Xaa Gly Xaa Cys Xaa Xaa
 1               5                  10                  15

Xaa Xaa Xaa Arg Xaa Phe Phe Asn Ile Phe Thr Arg Gln Cys Xaa Xaa
                20                  25                  30

Phe Xaa Xaa Gly Gly Cys Xaa Gly Asn Gln Asn Arg Phe Glu Ser Leu
            35                  40                  45

Glu Glu Cys Lys Lys Met Cys Thr Arg Asp
 50                  55
```